US009987256B2

(12) United States Patent
Sandona' et al.

(10) Patent No.: US 9,987,256 B2
(45) Date of Patent: Jun. 5, 2018

(54) CFTR CORRECTOR FOR THE TREATMENT OF GENETIC DISORDERS AFFECTING STRIATED MUSCLE

(71) Applicant: UNIVERSITA' DEGLI STUDI DI PADOVA, Padova (IT)

(72) Inventors: Dorianna Sandona', Polverara (IT); Roberta Sacchetto, Legnaro (IT); Elisa Bianchini, Vigasio (IT); Pompeo Volpe, Mira (IT); Romeo Betto, Padova (IT); Francesco Mascarello, Padova (IT)

(73) Assignee: UNIVERSITA' DEGLI STUDI DI PADOVA, Padova (IT)

( * ) Notice: Subject to any disclaimer, the term of this patent is extended or adjusted under 35 U.S.C. 154(b) by 64 days.

(21) Appl. No.: 14/647,773

(22) PCT Filed: Nov. 29, 2013

(86) PCT No.: PCT/EP2013/075158
§ 371 (c)(1),
(2) Date: May 27, 2015

(87) PCT Pub. No.: WO2014/086687
PCT Pub. Date: Jun. 12, 2014

(65) Prior Publication Data
US 2015/0328217 A1 Nov. 19, 2015

(30) Foreign Application Priority Data
Dec. 3, 2012 (IT) .......................... MI2012A002065

(51) Int. Cl.
*A61K 31/425* (2006.01)
*A61K 31/426* (2006.01)
*A61K 31/427* (2006.01)
*A61K 31/496* (2006.01)
*A61K 31/517* (2006.01)
*A61K 31/404* (2006.01)
*A61K 31/443* (2006.01)
*A61K 31/47* (2006.01)
*A61K 31/4709* (2006.01)
*A61K 31/472* (2006.01)
*A61K 31/506* (2006.01)

(52) U.S. Cl.
CPC .......... *A61K 31/426* (2013.01); *A61K 31/404* (2013.01); *A61K 31/427* (2013.01); *A61K 31/443* (2013.01); *A61K 31/47* (2013.01); *A61K 31/472* (2013.01); *A61K 31/4709* (2013.01); *A61K 31/496* (2013.01); *A61K 31/506* (2013.01); *A61K 31/517* (2013.01)

(58) Field of Classification Search
CPC ... A61K 31/426; A61K 31/425; A61K 31/427
See application file for complete search history.

(56) References Cited

U.S. PATENT DOCUMENTS

| 2006/0135549 A1 | 6/2006 | Graziani et al. |
| 2010/0010036 A1 | 1/2010 | Richard |
| 2011/0086899 A1 | 4/2011 | Winters et al. |

FOREIGN PATENT DOCUMENTS

| WO | 2007/056341 | | 5/2007 |
| WO | WO 2007091106 | * | 8/2007 |
| WO | 2009023509 A2 | | 2/2009 |

OTHER PUBLICATIONS

Sandona et al., Expert Rev Mol Med. Sep. 2009; 11: e28. pp. 1-27.*
Kirschner et al. (Sarcoglycanopathies. Hand Clin Neurol. 2011;101:41-46).*
Pan et al. (Mol Cells. Jun. 30, 2008;25(4):531-7. Epub May 6, 2008).*
Rowe et al. (Cold Spring Harb Perspect Med 2013;3:a009761).*
Robert, et al., "Structural analog of sildenafil identified as a novel corrector of hte F508del-CFTR trafficking defect", Molecular Pharmacology, American Society for Pharmacology and Experimental Therapeutics, US, vol. 73, No. 2, Feb. 1, 2008, pp. 478-489.
Benders, et al., "Ca 2+ homeostasis in Brody's disease a study in skeletal muscle and cultured cells and the effecdt of Dantrolene and verapamil", Aug. 1, 1994, pp. 741-748 http://ww.jci.org/articles/view/117393/pdf/render.
International Search Report and Written Opinion of PCT/EP2013/075158 of Feb. 17, 2014.
International Preliminary Report on Patentability of PCT/EP2013/075158 of Feb. 17, 2014.
Office Action of counterpart European Application No. 13801517.7-1466 dated Aug. 8, 2017.
Sandona' D. et al., "Sarcoglycanopathies: molecular pathogenesis and therapeutic prospects", Expert Reviews in Molecular Medicine, vol. 11, Sep. 1, 2009, pp. 1-27.

* cited by examiner

*Primary Examiner* — Jeffrey S Lundgren
*Assistant Examiner* — Chris Simmons
(74) *Attorney, Agent, or Firm* — Silvia Salvadori, P.C.; Silvia Salvadori

(57) ABSTRACT

The present invention relates to the use of CFTR correctors in the treatment of genetic disorders affecting striated muscle selected from sarcoglycanopathies, Brody's disease (BD) and the recessive forms of Cathecolaminergic Polymorphic Ventricular Tachycardia (CPVT).

4 Claims, 10 Drawing Sheets

CFTR CORRECTOR FOR THE TREATMENT OF GENETIC DISORDERS AFFECTING STRIATED MUSCLE

This application is a U.S. national stage of PCT/EP2013/075158 filed on 29 Nov. 2013, which claims priority to and the benefit of Italian Patent Application No. MI2012A002065 filed on 3 Dec. 2012, the contents of which are incorporated herein by reference in their entireties.

FIELD OF THE INVENTION

The present invention is directed to compounds and pharmaceutically acceptable salts thereof which are correctors of the cellular processing of cystic fibrosis transmembrane conductance regulator protein (hereinafter CFTR), for use in the treatment of genetic disorders affecting striated muscle selected from sarcoglycanopathies, Brody's disease (BD) and the recessive forms of Cathecolaminergic Polymorphic Ventricular Tachycardia (CPVT).

BACKGROUND OF THE INVENTION

Genetic disorders are pathologies caused by macroscopic alteration in chromosomes or microscopic lesions (point mutations, deletions or insertion) in genes. A genetic disorder is heritable when the genomic alteration is present in progenitors and can be transferred to the progeny. A genetic disorder is autosomal dominant when only one mutated copy of the gene (inherited by one progenitor) is necessary and sufficient for an organism to be affected, A genetic disorder is autosomal recessive when two copies of the gene (inherited by both progenitors) must be mutated for an organism to be affected. Over 4000 human diseases are due to single gene mutations, many of them affecting striated muscle tissues. Among these, sarcoglycanopathies are severe muscular dystrophies caused mainly by missense mutations in either α-, β-, γ- or δ sarcoglycan coding genes and are identified as Limb Girdle Muscular Dystrophy type 2D, 2E, 2C and 2F, respectively (Laval and Bushby 2004). Sarcoglycans (SGs) form a tetrameric complex linked to the dystrophin-associated protein complex and, in addition to the main structural role, they are involved in signaling [Barton 2006, Yoshida et al 1998]. In particular, α-SG is an ecto-ATPase enzyme [Sandonà et al 2004] possibly implicated in the extracellular ATP-dependent modulation of skeletal muscle contractility [Sandonà et al 2005]. Gene defects in a single sarcoglycan result in the absence or reduced expression of all SG subunits, with impaired tetramer formation and plasma membrane localization [Sandonà and Betto 2009]. About 75% of α-SG, 59% of β-SG, 40% of γ-SG and 57% of δ-SG genetic defects are missense mutations, known to generate full length proteins with single aminoacid substitution [Leiden Open Variation database]. Recently, it has been demonstrated that α-SG missense mutants are substrates of the ER quality control and are prematurely disposed of by the ubiquitin-proteasome system [Gastaldello et al 2008, Bartoli et al 2008].

In 1969, Brody first described in a human patient a muscular disorder characterized by an "exercise-induced impairment of muscle relaxation": muscle contraction was normal but relaxation appeared delayed after repetitive contractions [Brody 1969]. So far, Brody's disease (BD) is known as a rare inherited disorder of skeletal muscle due to a sarco(endo)plasmic reticulum $Ca^{2+}$-ATPase (SERCA) deficiency, resulting from missense, non sense mutations and in frame deletions of ATP2A1 gene, coding for SERCA1 isoform [Bertchtold et al 2000].

Three isoforms of SERCA proteins are differentially expressed by three genes. The SERCA1 isoform is expressed in fast-twitch (type 2) skeletal muscle. SERCA1 deficiency results in delayed muscle relaxation due to prolonged increase of calcium concentration in skeletal muscle fibres cytoplasm.

A muscular disorder defined as "congenital pseudomyotonia" (PMT) [Testoni et al 2008] has been described in bovine species. Clinical symptoms are exercise-induced muscle stiffness. DNA sequencing provided evidence of a missense mutations (R164H) in bovine ATP2A1 gene [Drögemüller et al 2008]. Moreover, biochemical results clearly demonstrated that cattle pathological muscles are characterized by a selective reduction in the expression level of SERCA1 protein, which accounts for the reduced $Ca^{2+}$-ATPase activity. By contrast, SERCA1 mRNA levels found in all affected animals were comparable with mRNA expression in normal samples [Sacchetto et al 2009].

For both Brody disease and cattle PMT a defect of ATP2A1 gene, resulting in selective reduction in SERCA1 expression level, has been indicated as causative of the disease and cattle PMT has been defined as the true counterpart of human Brody disease.

Since the mutations of ATP2A1 gene do not affect the transcription [Sacchetto et al 2009], it has been hypothesized that the resulting protein could be corrupted and could have an enhanced susceptibility to the protein degradation via ubiquitin-proteasomal pathway before being embedded into Sarcoplasmic Reticulum (SR) bilayer. This hypothesis turned out to be correct: results have demonstrated that SERCA1 R164H mutant is substrate of the quality control system and prematurely disposed of by the ubiquitin-proteasome pathway (Bianchini et al submitted for publication).

Catecholaminergic polymorphic ventricular tachycardia (CPVT) is an inherited, potentially fatal, arrhythmogenic disease characterized by stress- and/or emotion-induced life-threatening cardiac arrhythmias [Liu et al 2008]. Mutations in the cardiac ryanodine receptor (RyR2) gene have been associated with the autosomal dominant form of CPVT.1 whereas the autosomal recessive form of CPVT has been linked to mutations in CASQ2 and, recently, TRDN genes, encoding calsequestrin2 and triadin, respectively [Beard et al 2004; Roux-Buisson et al. 2012]. These proteins, together with RyR2 and junctin, form a quaternary macromolecular complex at the junctional SR of cardiomyocytes responsible for SR $Ca^{2+}$ release during cardiac muscle contraction. Investigations performed in knock-in models of dominant CPVT and recessive CPVT have demonstrated that abnormal $Ca^{2+}$ release induces cell-wide $Ca^{2+}$ waves, delayed after depolarizations and triggered activity, all of which lead to arrhythmogenesis [Liu et al 2009]. In the knock-in mouse model ($CASQ2^{R33Q/R33Q}$), drastic reduction of CASQ2 is accompanied by decrease of triadin (25%) and junctin (70%) without any change of the relative transcripts [Rizzi et al 2008]. It has been demonstrated that the strong reduction of the D307H CASQ2 mutant, also linked to the recessive form of human CPVT, is due to the activity of the ubiquitin-proteasome system. In the knock in mouse model $CASQ2^{D307H/D307H}$, the cardiac arrhythmia developed as consequence of CASQ2 mutant degradation, can be counteracted by systemic administration of the proteasome inhibitor Velcade that allows partial rescue of the mutant CSAQ2, i.e., 20% increase over not treated mice [Katz G et al 2013]. Similar results have been obtained by our group in the $CASQ2^{R33Q/R33Q}$ knock-in mouse by systemic delivery of Velcade (unpublished data). The T59R triadin mutant, recently identified in a CPVT patient, has been studied in both cellular and animal models suggesting it is prematurely disposed of by the ubiquitin-proteasome system of the cell [Roux-Buisson N et al. 2012].

Sarcoglycanopathies, BD and CPVT, even though affecting striated muscle, are very different genetic disorders both for symptoms and etiology. However, it is possible to recognize as common trait of these disorders the posttranscriptional removal of the mutated gene product because of folding problems, that leads to a de facto loss of function.

At present, there are no effective treatments for sarcoglycanopathies, Brody's disease (BD) or the recessive forms of Cathecolaminergic Polymorphic Ventricular Tachycardia (CPVT).

Recessive CPVT, for example, shows an incomplete response to β-blockers, that results in the recurrence of ventricular arrhythmias and cardiac arrest [Hayashi et al 2009]. BD patients are usually treated with dantrolene [Vattemi et al. 2010], a muscle relaxant (blocker of the dihydro-pyridine receptor-RyR complex), but due to liver toxicity, dantrolene is unsuitable for long-term treatment. Both gene and cell therapy strategies are under evaluation for the cure of sarcoglycanopathies and CPVT, but are far from being amenable of clinical trial [Daniel et al 2007; Denegri et al 2012]. Exon skipping strategy, very promising in Duchenne Muscular Dystrophy [Hoffman et al 2011] is not appropriate for sarcoglycanopathies, CPVT and BD since mutant proteins don't have dispensable sequence that could be skipped away. The use of molecules able to promote stop-codon-read-through is potentially applicable in these disorders when a nonsense mutation is present. However, in sarcoglycanopathies, for example, the percentage of missense mutations is considerably higher than that of other gene defects.

There are no drugs currently approved to treat sarcoglycanopathies, Brody's disease (BD) and the recessive forms of Cathecolaminergic Polymorphic Ventricular Tachycardia (CPVT) and therefore there is a great unmet need for the treatment of such diseases.

We have now found that small molecules known as "CFTR correctors" are able to reverse the pathological phenotype of sarcoglycanopathies BD and CPVT by promoting folding and proper targeting of the mutated misfolded proteins and thus can be used in the treatment of genetic disorders affecting striated muscle selected from sarcoglycanopathies, Brody's disease (BD) and the recessive forms of Cathecolaminergic Polymorphic Ventricular Tachycardia (CPVT).

REFERENCES

Beard N A, Laver D R, Dulhunty A F. Calsequestrin and the calcium release channel of skeletal and cardiac muscle. Prog Biophys Mol Biol 2004, 85:33-69.
Bartoli M, Gicquel E, Barrault L, Soheili T, Malissen M, Malissen B, Vincent-Lacaze N, Perez N, Udd B, Danos O, Richard I. Mannosidase I inhibition rescues the human α-sarcoglycan R77C recurrent mutation. Hum Mol Genet 2008, 17:1214-21.
Barton E R. Impact of sarcoglycan complex on mechanical signal transduction in murine skeletal muscle. Am. J. Physiol. 2006, 290:C411-419.
Berchtold M W, Brinkmeier H, Müntener M. Calcium ion in skeletal muscle: its crucial role for muscle function, plasticity, and disease. Physiol Rev 2000, 80:1215-65.
Brody I A. Muscle contracture induced by exercise: a syndrome attributable to decreased relaxing factor. New Eng. J Med 1969, 281:187-92.
Daniel N, Richard I, Bartoli M. Ins and outs of therapy in limb girdle muscular dystrophies. Int. J. Biochem. Cell Biol. 2007, 39, 1608-24.
Denegri M, Avelino Cruz J E, Boncompagni S, De Simone S A, Auricchio A, Villani L. Volpe P, Protasi F, Napolitano C, Priori S G. Gene therapy rescues molecular, structural and electrical defects in a model of genetic arrhythmias. Circ Res. 2012, 110:663-8.
Drögemüller C, Drögemüller M, Leeb T, Mascarello F, Testoni S, Rossi M, Gentile A, Damiani E, Sacchetto R. Identification of a missense mutation in the bovine ATP2A1 gene in congenital pseudomyotonia of Chianina cattle: an animal model of human Brody disease. Genomics 2008, 92: 474-77.
Gastaldello S, D'Angelo S, Franzoso S, Fanin M, Angelini C, Betto R, Sandonà D. Inhibition of proteasome activity promotes the correct localization of disease-causing α-sarcoglycan mutants in HEK-293 cells constitutively expressing β, γ-, and δ-sarcoglycan. Am J Pathol 2008, 173:170-81.
Hayashi M, Denjoy I, Extramiana F, Maltret A, Buisson N R, Lupoglazoff J M, Klug D, Hayashi M, Takatsuki S, Villain E, Kamblock J, Messali A, Guicheney P, Lunardi J, Leenhardt A. Incidence and risk factors of arrhythmic events in catecholaminergic polymorphic ventricular tachycardia. Circulation. 2009, 119:2426-34.
Hoffman E P, Bronson A, Levin A A, Takeda S, Yokota T, Baudy A R, Connor E M. Restoring dystrophin expression in duchenne muscular dystrophy muscle progress in exon skipping and stop codon read through. Am J Pathol. 2011, 179:12-22.
Katz G, Shainberg A, Hochhauser E, Kurtzwald-Josefson E, Issac A, El-Ani D, Aravot D, Afek A, Seidman J G, Seidman C E, Eldar M, Arad M. The role of mutant protein level in autosomal recessive catecholamine dependent polymorphic ventricular tachycardia (CPVT2). Biochem Pharmacol. 2013 Dec. 1; 86(11):1576-83. Epub 2013 Sep. 23.
Laval S H and Bushby K M D. Limb-girdle muscular dystrophies—from genetics to molecular pathology. Neuropathology and Applied Neurobiology 2004, 30: 91-105.
Liu N, Ruan Y, Priori S G. Catecholaminergic polymorphic ventricular tachycardia. Prog Cardiovasc Dis. 2008, 51:23-30.
Liu N, Rizzi N, Boveri L, Priori S G. Ryanodine receptor and calsequestrin in arrhythmogenesis: what we have learnt from genetic diseases and transgenic mice. J Mol Cell Cardiol. 2009, 46:149-159.
Rizzi N, Liu N, Napolitano C, Nori A, Turcato F, Colombi B, Bicciato S, Arcelli D, Spedito A, Scelsi M, Villani L, Esposito G, Boncompagni S, Protasi F, Volpe P, Priori S G. Unexpected structural and functional consequences of the R33Q homozygous mutation in cardiac calsequestrin: A complex arrhythmogenic cascade in a knock in mouse model. Circ Res 2008, 103:298-306.
Roux-Buisson N, Cacheux M, Fourest-Lieuvin A, Fauconnier J, Brocard J, Denjoy I, Durand P, Guicheney P, Kyndt F, Leenhardt A, Le Marec H, Lucet V, Mabo P, Probst V, Monnier N, Ray P F, Santoni E, Trémeaux P, Lacampagne A, Fauré J, Lunardi J, Marty I. Absence of triadin, a protein of the calcium release complex, is responsible for cardiac arrhythmia with sudden death in human. Hum Mol Genet. 2012, 21:2759-67.

Sacchetto R, Testoni S. Gentile A. Damiani E, Rossi M, Liguori R, Drögemüller C, Mascarello F. A defective SERCA1 protein is responsible for congenital pseudomyotonia in Chianina cattle. Am J Pathol 2009, 174:565-73.

Sandonà D, Gastaldello S, Martinello T, Betto R. Characterization of the ATP-hydrolyzing activity of α-sarcoglycan. Biochem J 2004, 381:105-12.

Sandonà D, Danieli-Betto D, Germinario E, Biral D, Martinello T, Lioy A, Tarricone E, Gastaldello S, Betto R. The T-tubule membrane ATP-operated P2X4 receptor influences contractility of skeletal muscle. FASEB Journal 2005, 19:1184-1186.

Sandonà D, Betto R. Sarcoglycanopathies: molecular pathogenesis and therapeutic prospects. Expert Rev Mol Med 2009, 11:e28.

Testoni S, Boni P, Gentile A. Congenital pseudomyotonia in Chianina cattle. Vet Rec 2008, 163:252.

Vattemi G, Gualandi F, Oosterhof A, Marini M, Tonin P, Rimessi P, Neri M, Guglielmi V, Russignan A, Poli C, van Kuppevelt T H, Ferlini A, Tomelleri G. Brody Disease: Insights Into Biochemical Features of SERCA1 and Identification of a Novel Mutation. J Neuropathol Exp Neurol 2010, 69:246-52.

Yoshida T, Pan Y, Hanada H, Iwata Y, Shigekawa M. Bidirectional signaling between sarcoglycans and the integrin adhesion system in cultured L6 myocytes. J. Biol. Chem. 1998, 273: 1583-1590.

SUMMARY OF THE INVENTION

The solution provided by the present invention is the use of CFTR correctors that promote folding and trafficking of CFTR, in the treatment of genetic disorders affecting striated muscle selected from sarcoglycanopathies, Brody's disease (BD) and the recessive forms of Cathecolaminergic Polymorphic Ventricular Tachycardia (CPVT).

Thus, the present invention provides a CFTR corrector for use in the treatment of genetic disorders affecting striated muscle selected from sarcoglycanopathies, Brody's disease (BD) and the recessive forms of Cathecolaminergic Polymorphic Ventricular Tachycardia (CPVT).

In another aspect, the present invention provides a method of treatment of genetic disorders affecting striated muscle selected from sarcoglycanopathies, Brody's disease (BD) and the recessive forms of Cathecolaminergic Polymorphic Ventricular Tachycardia (CPVT) comprising administering a safe and effective amount of a CFTR corrector to a patient in need thereof.

In another aspect, the present invention provides pharmaceutical compositions comprising a CFTR corrector and one or more pharmaceutically acceptable excipients for use in the treatment of genetic disorders affecting striated muscle selected from sarcoglycanopathies, Brody's disease (BD) and the recessive forms of Cathecolaminergic Polymorphic Ventricular Tachycardia (CPVT).

DETAILED DESCRIPTION OF THE INVENTION

Definitions

Figure 1:
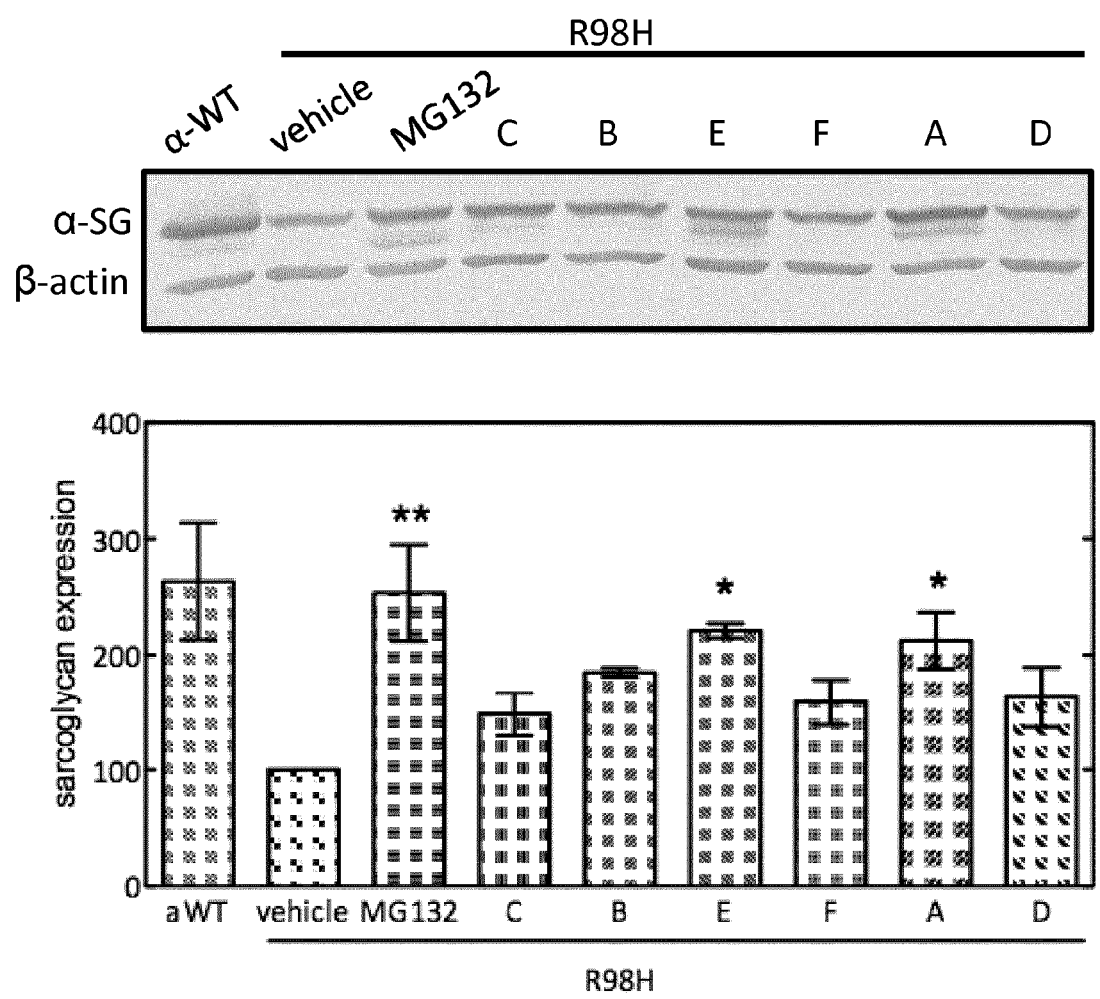
FIG. 1 CFTR correctors (Compounds A to F) promote the rescue of R98H mutant of alpha-sarcoglycan in HEK293 cell model. Alpha-sarcoglycan (α-SG) protein level has been determined by western blot (a representative experiment is shown in the top panel) on total protein content purified from cells expressing the R98H mutant treated with either CFTR correctors (compound A, B, C, D, E and F as indicated), MG132 (proteasome inhibitor) used as positive control, or correctors vehicle (DMSO) used as negative control. Cells expressing the wild type form of alpha-sarcoglycan have also been analyzed, for comparison. To normalize protein content, the expression of β-actin has been used as an internal marker. The graph in the lower part of the figure shows the average values (+/− standard error) of alpha-sarcoglycan expression determined by densitometric analyses of at least three independent experiments. Values are expressed as percentage of the alpha-sarcoglycan protein content present in cells expressing the R98H mutant treated with vehicle. **, P≤0.01; *, P≤0.05.

The term "CFTR" as used herein means cystic fibrosis transmembrane regulator or a mutation thereof capable of regulator activity, including, but not limited, to ΔF508 CFTR.

The term "CFTR correctors" as used herein means a molecule, correcting the defective cellular processing, able to increase the number of CFTR in a cellular membrane.

The term "SERCA1" as used herein is the acronym of sarco(endo)plasmic reticulum $Ca^{2+}$-ATPase isoform 1.

The term "CASQ2" as used herein is the acronym of calsequestrin isoform 2.

"Protein folding" as used herein means the process by which a polypeptide chain folds to a specific three-dimensional protein structure assuming its functional shape or conformation.

Protein trafficking is the mechanism by which proteins destined either to the plasma membrane or secretion transit through Endoplasmic Reticulum, Golgi apparatus and by transport vesicles reach the final destination.

Misfolded protein as used herein means a protein unable to reach its functional shape or conformation because of the presence of missing or incorrect amino acids. The term "missense mutation" as used herein means a point mutation in which a single nucleotide is changed, resulting in a codon that codes for a different amino acid, thus for example: R98H mutant of α-sarcoglycan means that at position 98 of α-sarcoglycan sequence the amino acid R (Arginine) has been changed in H (Histidine); V247M mutant of α-sarcoglycan means that at position 247 of α-sarcoglycan sequence the amino acid V (Valine) has been changed in M (Methionine); R33Q mutant of CASQ2 means that at position 33 of calsequestrin 2 the amino acid R (Arginine) has been changed in Q (Glutamine); R164H mutant of SERCA1 means that at position 164 of SERCA1 sequence the amino acid R (Arginine) has been changed in H (Histidine).

The term "non sense mutation" as used herein means a point mutation in which a single nucleotide is changed, resulting in a stop codon.

The term "in frame deletion" as used herein means a genetic mutation caused by deletions of three or multiple of three nucleotides from a DNA sequence leading to the loss of one of more amino acids with no other consequence on protein sequence.

The term "ubiquitin" refers to a small regulatory protein that can be attached to proteins and label them for destruction through proteasome.

The term "proteasome" refers to a macromolecular protein complex responsible of the ATP dependent degradation of ubiquitin tagged proteins.

The term "primary culture" as used herein means cells either of human or animal origin prepared by mechanical or enzymatic dissociation of a specific tissue or bioptic fragment of tissue.

The term "muscular biopsy" as used herein means a fragment of skeletal muscle tissue removed from either a human or animal subject that can be used to diagnose a diseases involving muscle tissue and that can be also used, after acquisition of informed consent, for research experiments.

The term "disease animal model" means a living, non-human animal that, because of naturally occurring variation of its genome or because its genome has been artificially modified, develops a disease similar to a human condition.

The term "Knock out (KO) mouse" means a genetically engineered mouse in which an existing gene has been inactivated, or "knocked out," by replacing it or disrupting it with an artificial piece of DNA. The loss of gene activity often causes changes in mouse's phenotype and can lead to the development of a disease similar to a human condition.

The term "Knock in (KI) mouse" as used herein means a genetically engineered mouse in which the protein coding region of a gene has been replaced by the same coding region containing point mutations. The expression of the mutated gene can causes changes in mouse's phenotype and can lead to the development of a disease similar to a human condition.

The term LGMD-2D means Limb Girdle Muscular Dystrophy type 2D (sarcoglycanopathy) caused by mutations of the SGCA gene coding for alpha-sarcoglycan.

The term LGMD-2E means Limb Girdle Muscular Dystrophy type 2E (sarcoglycanopathy) caused by mutations of the SGCB gene coding for beta-sarcoglycan.

The term LGMD-2C means Limb Girdle Muscular Dystrophy type 2C (sarcoglycanopathy) caused by mutations of the SGCG gene coding for gamma-sarcgoglycan.

The term LGMD-2F means Limb Girdle Muscular Dystrophy type 2F (sarcoglycanopathy) caused by mutations of the SGCD gene coding for delta-sarcoglycan.

As used herein, "treat" in reference to a disorder means: (1) to ameliorate the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

"Treatment," thus, for example, covers any treatment of a condition or disease in a mammal, particularly in a human, and includes: (a) preventing the condition or disease, disorder or symptom thereof from occurring in a subject which may be predisposed to the condition or disease or disorder but has not yet been diagnosed as having it; (b) inhibiting the condition or disease, disorder or symptom thereof, such as, arresting its development; and (c) relieving, alleviating or ameliorating the condition or disease or disorder or symptom thereof, such as, for example, causing regression of the condition or disease or disorder or symptom thereof.

As used herein, "safe and effective amount" in reference to CFTR correctors or a pharmaceutically acceptable salt thereof, or other pharmaceutically-active agent, means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect.

As used herein, "patient" refers to a human (including adults and children) or other animal affected by a disease. In one embodiment, "patient" refers to a human.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of a compound of use according to the invention or a pharmaceutically acceptable salt thereof when administered to a patient and interactions which would result in pharmaceutical compositions that are not pharmaceutically acceptable are avoided. In addition, each excipient must of course be pharmaceutically-acceptable eg of sufficiently high purity.

As used herein, the term "pharmaceutically acceptable salt" refers to a salt that retains the desired biological activity of the compound and exhibits minimal undesired toxicological effects. Pharmaceutically acceptable salts of compounds may be used to impart greater stability or solubility to a molecule thereby facilitating formulation into a dosage form.

In one embodiment, the present invention provides correctors of the cellular processing of cystic fibrosis transmembrane conductance regulator protein (hereinafter CFTR), in the treatment of genetic disorder affecting striated muscle selected from sarcoglycanopathies, Brody's disease (BD) and the recessive forms of Cathecolaminergic Polymorphic Ventricular Tachycardia (CPVT).

In one embodiment the genetic disorders affecting striated muscle are sarcoglycanopathies or Brody's disease (BD).

CFRT correctors of use in the present invention are fully described, for example in U.S. Pat. No. 8,227,615, U.S. Pat. No. 8,143,295, U.S. Pat. No. 7,977,322, U.S. Pat. No. 7,939,558, U.S. Pat. No. 7,645,789 U.S. Pat. No. 6,770,663; in US patent application Nos US20120184583, US20120101143, US20120004405, US2011257223, US20110281873, US20110257223, US20110245322, US20110201544, US20110177999, US20110071206, US20110060024, US20100331297, US20100273839, US20100144798, US20100113555, US20090246137, US20090253736, US20090221597, US20090131492, US20080319008, US20080318984, US20080176899, US20080161371, US20060052358, US20050113423; US20050176761 in European Patent No EP1912983 B1; in Japanese application No 2009057364;

in PCT international patent applications WO2012021974 WO2012036573 WO2011137427, WO2011133956, WO2011133953, WO2011133951, WO2011008931, WO2010151747, WO2010068863, WO2010066912, WO2010048125, WO2010054138, WO2009123896, WO2009105234, WO2009108657, WO2009062118, WO2009051909, WO2009051910, WO2009039567, WO2009023509, WO2008141119, WO2008127399, WO2007117715, WO2007075946, WO2007021982, WO2007056341, WO2006101740, WO2006099256, WO2006052821, WO2005120497, WO2005075435, WO2004080972, WO2004111014.

The preparation of such compounds is fully described in the afore-mentioned publications the subject matter of which is incorporated herein by reference in its entirety.

A representative first class of CFTR correctors is as disclosed in WO2009051909 as a compound of formula (I)

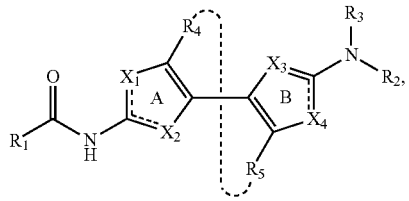

(I)

or the salts, solvates, hydrates, and prodrug forms thereof, and stereoisomers thereof, wherein:

A and B are aromatic rings each independently selected from thiazole and oxazole, with X1, X2, X3 and X4 being heteroatoms selected from N, O and S, with each dotted line connecting X1 to X2 within ring A and X3 to X4 within ring B being a single or double bond provided that when one bond is a double bond then the other bond is a single bond, and with the dotted line connecting R4 and R5 indicating rotational isomers around the solid line bond connecting rings A and B.

R1 is a substituted or unsubstituted group selected from aliphatic and aryl, with the proviso that when R1 is an unsubstituted phenyl then R3 or R5 is other than hydrogen;

R2 is a substituted or unsubstituted aryl;

R3 is hydrogen or substituted or unsubstituted aliphatic; and

R4 and R5 are each independently hydrogen, a substituted or unsubstituted lower aliphatic, or form a bridge comprising a heteroatom or a substituted or unsubstituted lower aliphatic chain, with the dotted line connecting R4 and R5 further indicating either no bridge for unbridged R4 and R5 or said bridge for bridged R4 and R5.

A particularly preferred compound of formula (I) is

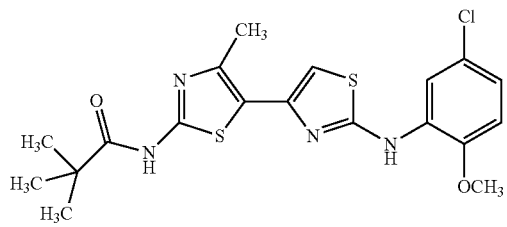 [SMILES: COc1ccc(Cl)cc1Nc1nc(-c2sc(NC(=O)C(C)(C)C)nc2C)cs1]

N-(2-(5-chloro-2-methoxyphenylamino)-4'-methyl-4,5'-bithiazol-2'-yl)pivalamide. (hereinafter Compound A).

A representative second class of CFTR correctors is as disclosed in WO2004111014 as a compound of formulae (V-A, V-B and V-E)

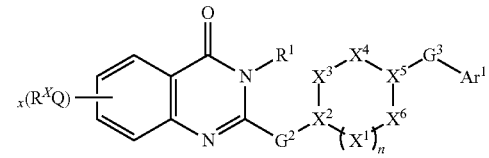

V-A

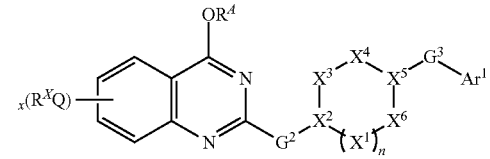

V-B

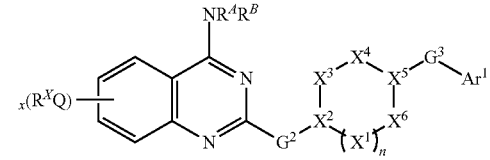

V-E or a pharmaceutically acceptable salt thereof, wherein RA and RB are each independently V-RV, or RA and RB, taken together with the nitrogen atom, form an optionally substituted 3-12 membered saturated, partially unsaturated, or fully unsaturated monocyclic or bicyclic ring having 0-4 heteroatoms independently selected from nitrogen, oxygen, or sulfur, wherein V is a bond or is an optionally substituted C1-C6 alkylidene chain wherein up to two methyleneunits of V are optionally and independently replaced by —CO—, —CS—, —COCO—, —CONR'—, —CONR'NR'—, —CO2-, —OCO—, —NR'CO2-, —O—, —NR'CONR'—, —OCONR'—, —NR'NR', —NR'NR'CO—, —NR'CO—, —S—, —SO, —SO2-, —NR'—, —SO2NR'—, NR'SO2-, —NR'SO2NR'—, and each occurrence of RV is independently R', halogen, NO2, or CN, and wherein RA and RB, or any ring formed by RA and RB taken together with the nitrogen atom, are optionally and independently substituted by q occurrences of U-RU, wherein q is 0-5;

U is a bond or is an optionally substituted C1-C6 alkylidene chain wherein up to two methylene units of U are optionally and independently replaced by —CO—, —CS—, —COCO—, —CONR'—, —CONR'NR'—, —CO2-, —OCO—, —NR—CO2-, —O—, —NR'CONR'—, —OCONR'—, —NR'NR', —NR'NR'CO—, —NR'CO—, —S—, —SO, —SO2-NR'—, —SO2NR'—, —NR'SO2-, —NR'SO2NR'—, and each occurrence of RU is independently R', halogen, NO2, or CN;

R1 is absent or is Y-RY;

Y is a bond or is an optionally substituted C1-C6 alkylidene chain wherein up to two methylene units of Y are optionally and independently replaced by —CO—, —CONR—, —O— —NRCO—, —S—, —SO2-, —NR—, —SO2NR—, or —NRSO2-, and each occurrence of RY is independently R', OR', SR', N(R')2, halogen, NO2, or CN, provided that when R1 is present, it is always bonded to the nitrogen atom through a carbon atom; each occurrence of R is independently selected from hydrogen or an optionally substituted C1-8 aliphatic group; and each occurrence of R' is independently selected from hydrogen or an optionally substituted group selected from a C1-C8 aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', or two occurrences of R, are taken together with the atoms) to which they are bound to form an optionally substituted 3-12 membered saturated, partially unsaturated, or fully unsaturated monocyclic or bicyclic ring having 0-4 heteroatoms independently selected from nitrogen, oxygen, or sulfur; Q is a bond or is an optionally substituted C1-C6 alkylidene chain wherein up to two methylene units of Q are optionally and independently replaced by —CO—, —CS—, —COCO—, —CONR—, —CONRNRCO2-, —OCO—, —NRCO2-, —O—, —NRCONR—, —OCONR—, —NRNR, —NRNRCO—, —NRCO—, —S—, —SO, —SO2-, —NR—, —SO2NR—, —NRSO2-, —NRSO2NR—, and each occurrence of RX is independently R', halogen, NO2, or CN; wherein x is 0-5; wherein G2 and G3 are each independently absent or an optionally substituted C1-C6 alkylidene chain, wherein one or two methylene units are optionally and independently replaced with —CO—, —CS—, —SO—, —SO2-, —NR'—, NSO2R')—, NCOR')—, —O—, or —S—, and wherein one or two hydrogen atoms of one or more methylene units are optionally substituted with R'Ar1 is absent or is a 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein Ar1 is optionally substituted with m independent occurrences of WRW, wherein m is 0-5 and W is a bond or is an optionally substituted C1-C6 alkylidene chain wherein up to two methylene units of T are optionally and independently replaced by —CO—, —CS—, —COCO—, —CONR—, —CONRNR—, —CO2-, —OCO—, —NRCO2-, —O—, —NRCONR—, —OCONR—, —NRNR, —NRNRCO—, —NRCO—, —S—, —SO, —SO2-, —NR—, —SO2NR—, —NRSO2-, —NRSO2NR—, and each occurrence of RW is independently R', halogen, NO2, or CN; wherein n is 0, 1, or 2; X2 and X5 are each independently CR' or N; and each occurrence of X1, when present, and X3, X4 and X6 are each independently, as valency and stability permit, C(R')2, —O—, —NR—, S, C=O, or C=S.

A particularly preferred compounds of formula (V-B) is

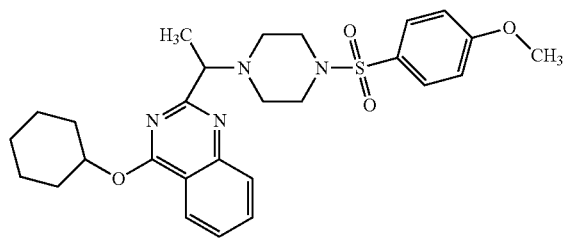 [SMILES: COc1ccc(S(=O)(=O)N2CCN(C(C)c3nc(OC4CCCCC4)c4ccccc4n3)CC2)cc1]

4-Cyclohexyloxy-2-{1-[4-(4-methoxy-benzensulfonyl)-piperazin-1-yl]-ethyl}-quinazoline (hereinafter Compound B), individual stereoisomers thereof or a pharmaceutically acceptable salt thereof.

A particularly preferred compounds of formula (V-E) is

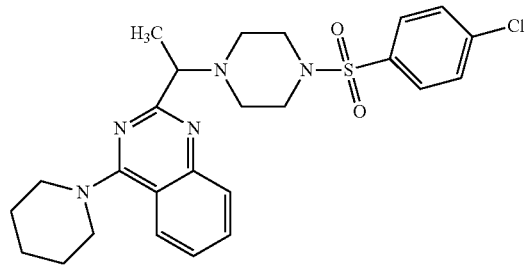 [SMILES: CC(c1nc(N2CCCCC2)c2ccccc2n1)N1CCN(S(=O)(=O)c2ccc(Cl)cc2)CC1]

2-{1-[4-(4-Chloro-benzensulfonyl)-piperazin-1-yl]ethyl}-4-piperidin-1-yl-quinazoline (hereinafter Compound C), individual stereoisomers thereof or a pharmaceutically acceptable salt thereof.

A representative third class of CFTR correctors is as disclosed in WO2007021982 as a compound of formula (III) or (IIIa)

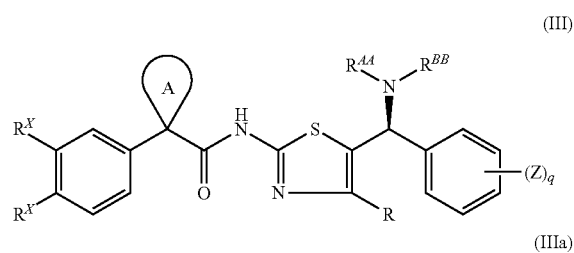

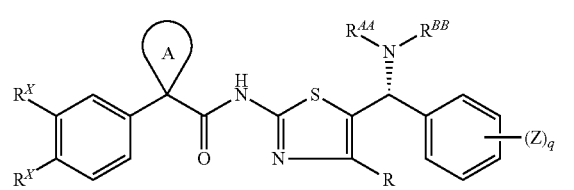

or a pharmaceutically acceptable salt thereof, wherein: each $R^x$ is independently hydrogen, halo, CF3, C1-C4 alkyl, or —OC1-C4 alkyl; provided that both $R^x$ are not simultaneously hydrogen; or the two $R^x$, taken together form ring (a):

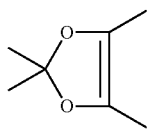

(a)

X is CH2, CF2, CH2-CH2, or CF2-CF2; ring A is 3-7 membered monocyclic cycloalkyl ring;

$R^{AA}$ and $R^{BB}$, taken together with the nitrogen atom, form a pyrrolidinyl ring substituted with OR';

R' is hydrogen or C1-C6 aliphatic, wherein up to two carbon units of said aliphatic are optionally and independently replaced by —CO—, —CS—, —COCO—, —CONR—, —CONRNR—, —CO2-, —OCO—, —NRCO2-, —O—, —NRCONR—, —OCONR—, —NRNR, —NRNRCO—, —NRCO—, —S—, —SO, —SO2-, —NR—, —SO2NR—, NRSO2-, or —NRSO2NR—;

R is hydrogen or C1-C6 aliphatic;

Z is an electron withdrawing substituent; and q is 0-3.

A particularly preferred compound of formula (III) is

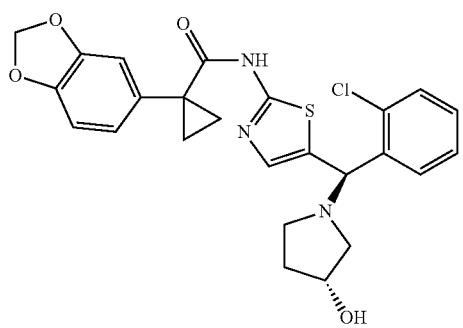 [SMILES: O=C(Nc1ncc([C@@H](c2ccccc2Cl)N2CC[C@@H](O)C2)s1)C1(c2ccc3c(c2)OCO3)CC1]

1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (hereinafter Compound D) or a pharmaceutically acceptable salt thereof.

A representative fourth class of CFTR correctors is as disclosed in WO2006101740 as a compound of formula (II):

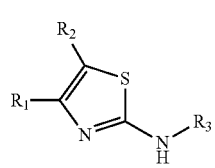

(II)

wherein R1 is independently selected from a substituted or unsubstituted phenyl group, R2 is independently selected from a hydrogen or an alkyl group, R3 is independently selected from a substituted or unsubstituted phenyl group, a substituted or unsubstituted heteroaromatic group, a substituted amino group, a substituted acyl group; or a pharmaceutically acceptable derivative thereof, as an individual stereoisomer or a mixture thereof; or a pharmaceutically acceptable salt thereof.

In one embodiment, R1 is chosen from an unsubstituted phenyl group, a unsubstituted biphenyl group, a 3-, 4-di(methyl)phenyl group, a 4-(methyl)phenyl group, a 3-, 4-di(methoxy)phenyl group, a 3-, 4-di(hydroxy)phenyl group, a 4-(bromo)phenyl group, a 4-(propene)phenyl group, a 3-(methyl)-4-(methoxy)phenyl group, or a 3-(nitro)-4(methyl)phenyl group.

In another embodiment, R2 is chosen from a hydrogen or a methyl group. In yet another embodiment, R3 is chosen from a unsubstituted phenyl group, as a 3-(chloro)phenyl group, a 4-(fluoro)phenyl group, a 2-(methyl)phenyl group, a 2-(ethoxy)phenyl group, a 2-,5-di(methoxy)-4-(chloro) phenyl group, a 4-(acetamide)phenyl group, a unsubstituted pyrimidine group, a 3-(methyl)pyridine group, a di(methyl) butylideneamine group, an acyl-thiophene group, an acyl(4-t-butyl-phenyl)group, or an acyl-methylthio-imidazol-5-phenyl group.

In representative embodiments, the compound is chosen from:

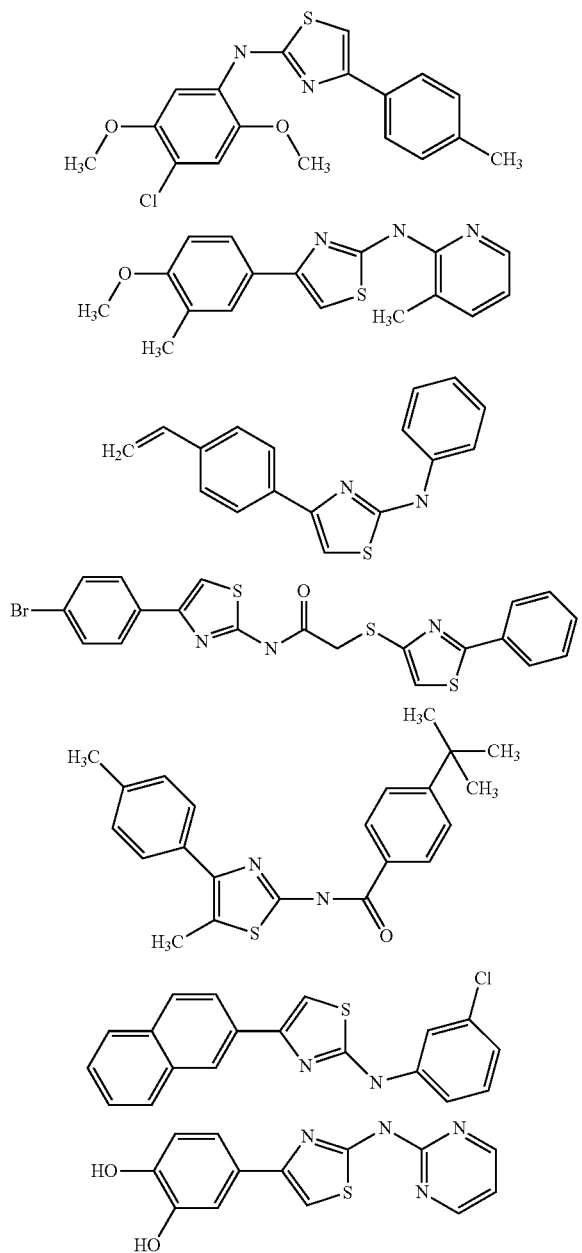

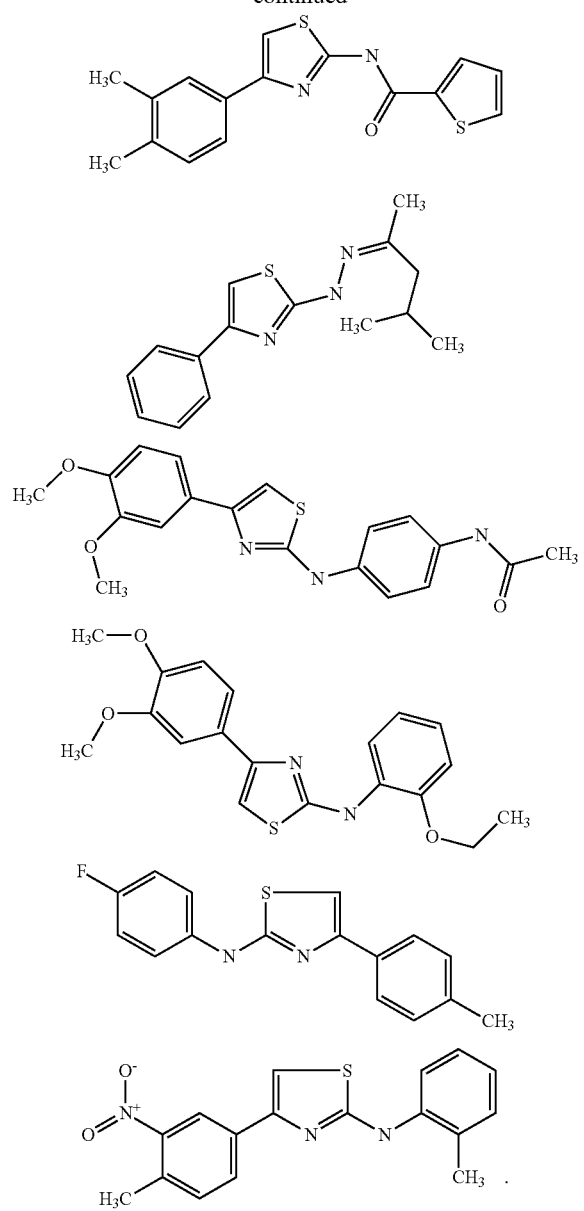

A particularly preferred compound of formula (II) is

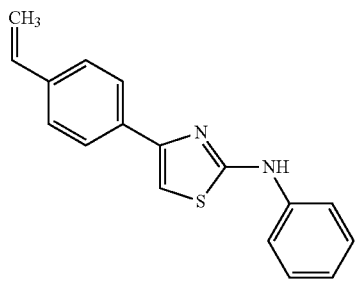 [SMILES: C=Cc1ccc(-c2csc(Nc3ccccc3)n2)cc1]

N-phenyl-4-(4-vinylphenyl)thiazol-2-amine (hereinafter Compound S) or a pharmaceutically acceptable salt thereof.

or as a compound of formula (III):

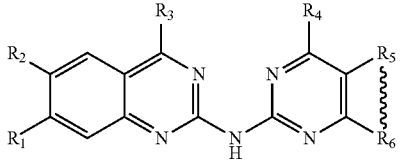

wherein R1 is chosen from a hydrogen, an alkyl group, or an alkoxy group;

R2 is chosen from a hydrogen, an alkyl group, or an alkoxy group;

R3 is an alkyl group;

R4 is chosen from a hydroxyl group or a carbonyl group;

R5 and R6 are chosen from a fused cycloalkyl group, a hydrogen, an alkyl group, or a substituted or unsubstituted phenyl group; or a pharmaceutically acceptable derivative thereof, as an individual stereoisomer or a mixture thereof; or a pharmaceutically acceptable salt thereof.

In one embodiment, R1 chosen from a hydrogen, a methyl group, an ethyl group, a methoxy group, or an ethoxy group. In another embodiment, R2 is chosen from a hydrogen, a methyl group, an ethyl group, a methoxy group, or an ethoxy group. In yet another embodiment, R3 is chosen from a methyl group or an ethyl group. In yet another embodiment, R4 is chosen from a hydroxyl group or a carbonyl group. In yet another embodiment, R5 is chosen from a hydrogen, a methyl group, an ethyl group, a unsubstituted phenyl group, or a 2-methylthio-1H-benzoimidazole group. In yet another embodiment, R6 is chosen from a hydrogen, a methyl group, an ethyl group, a unsubstituted phenyl group, or a 2-methylthio-1H-benzoimidazole group. In yet another embodiment, R5 and R6 are a fused cyclopenyl group.

In representative embodiments, the compound is chosen from:

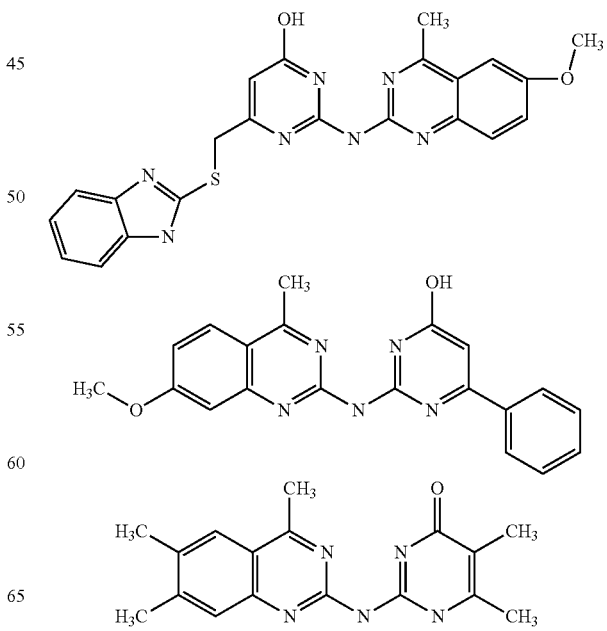

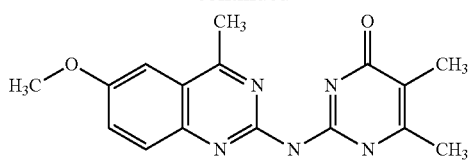

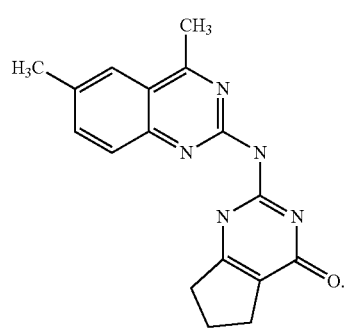

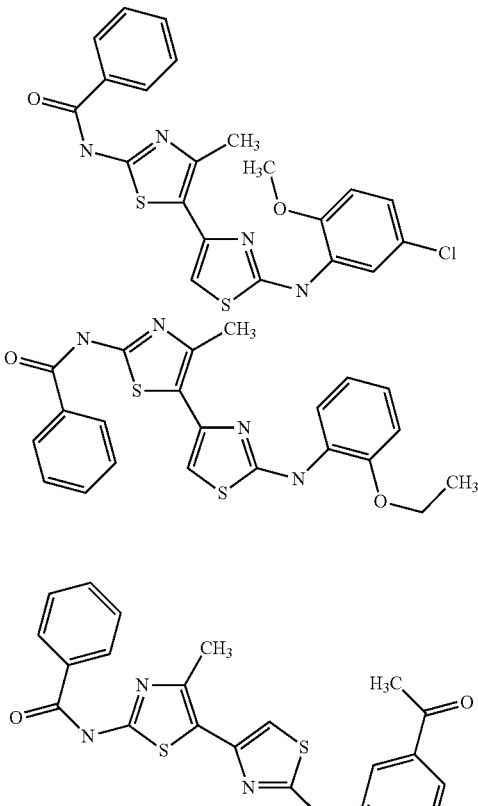

A particularly preferred compound of formula (III) is

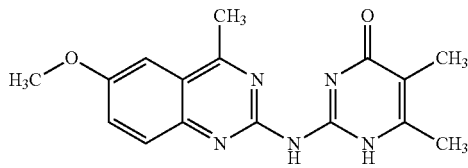

2-(6-methoxy-4-methylquinazolin-2-ylamino)-5,6-dimethylpyrimidin-4(1H)-one (hereinafter Compound T) or a pharmaceutically acceptable salt thereof.

or as a compound of formula (IV):

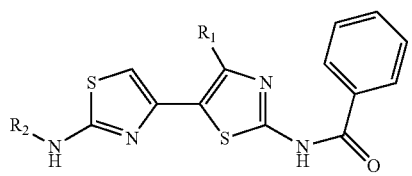

(IV)

wherein R1 is a alkyl group and R2 is a substituted or unsubstituted phenyl group; or a substituted or unsubstituted phenyl group; or a pharmaceutically acceptable derivative thereof, as an individual stereoisomer or a mixture thereof;

In one embodiment, R1 is a methyl group. In another embodiment, R2 is chosen from a 3-(nitro)phenyl group, a 2-methoxyphenyl, a 2-ethoxyphenyl, a 1-phenylethyl-1-one group, or a 3-chloro-6-methoxyphenyl group.

In representative embodiments, the compound is chosen from:

A particularly preferred compound of formula (IV) is selected from

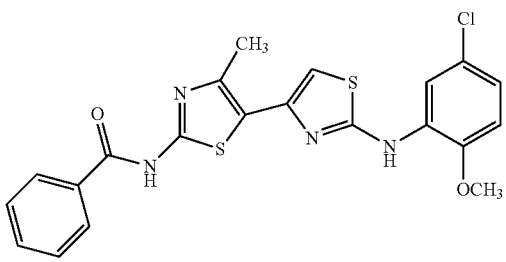 [SMILES: COc1ccc(Cl)cc1Nc1nc(-c2sc(NC(=O)c3ccccc3)nc2C)cs1]

N-[2-(5-Chloro-2-methoxy-phenylamino)-4'-methyl-[4,5'] bithiazolyl-2'-yl]-benzamide (hereinafter Compound E);

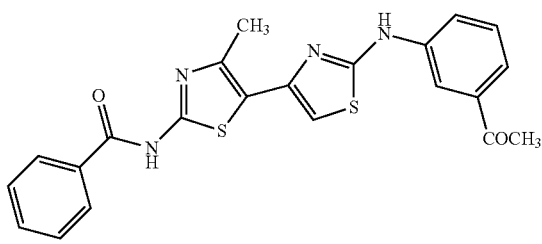 [SMILES: CC(=O)c1cccc(Nc2nc(-c3sc(NC(=O)c4ccccc4)nc3C)cs2)c1]

N-(2-(3-acetylphenylamino)-4'-methyl-4,5'-bithiazol-2'-yl)-benzamide (hereinafter compound Q);

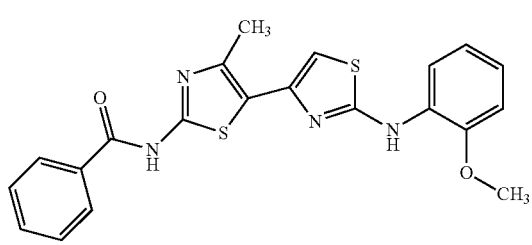 [SMILES: COc1ccccc1Nc1nc(-c2sc(NC(=O)c3ccccc3)nc2C)cs1]

N-(2-(2-methoxyphenylamino)-4'-methyl-4,5'-bithiazol-2'-yl)-benzamide (hereinafter Compound R);
or a pharmaceutically acceptable salt thereof.
or as a compound of formula (V):

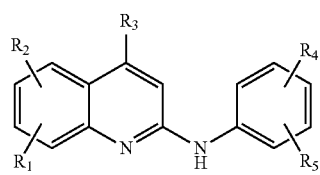

(V)

wherein R1 is chosen from a hydrogen, or an alkyl group; R2 is chosen from a hydrogen, or an alkyl group; R3 is an alkyl group; R4 is chosen from a hydrogen, an alkyl group, an alkoxy group, or a halogen group; and R5 is chosen from a hydrogen, an alkyl group, an alkoxy group, or a halogen group; or a pharmaceutically acceptable derivative thereof, as an individual stereoisomer or a mixture thereof; or a pharmaceutically acceptable salt thereof.

In one embodiment, R1 is chosen from a hydrogen or a methyl group. In another embodiment, R2 is chosen from a hydrogen or a methyl group. In yet another embodiment, R3 is chosen from a hydrogen or a methyl group. In yet another embodiment, R4 is chosen from a hydrogen, a brominde group, a chloride group, or a methoxyl group. In yet another embodiment, R5 is chosen from a hydrogen, a brominde group, a chloride group, or a methoxyl group. In representative embodiments, the compound is chosen from:

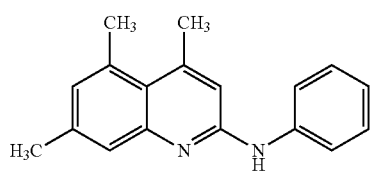

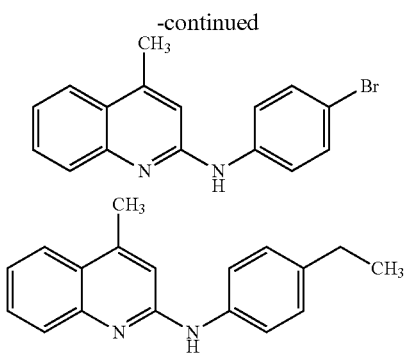

A particularly preferred compound of Formula (V) is selected from

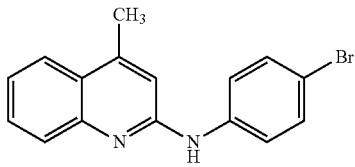 [SMILES: Cc1cc(Nc2ccc(Br)cc2)nc2ccccc12]

N-(4-bromophenyl)-4-methylquinolin-2-amine (hereinafter Compound I);

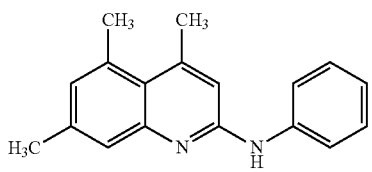 [SMILES: Cc1cc(C)c2c(C)cc(Nc3ccccc3)nc2c1]

4,5,7-trimethyl-N-phenylquinolin-2-amine (hereinafter Compound H); or a pharmaceutically acceptable salt thereof.

A representative fifth class of CFTR correctors is as disclosed in WO2007056341 a compound of formula V-A-i or V-B-i:

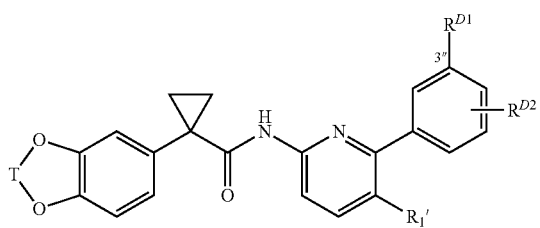

VI-A-i

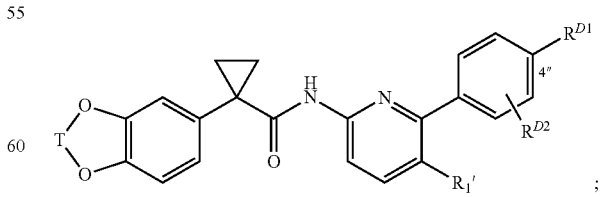

VI-A-ii or a pharmaceutically acceptable salt thereof, wherein
T is —CH2-, —CF2-, or —C(CH3)2-.
Ri' is selected in several embodiments from the group consisting of H, C1-6 aliphatic, halo, CF3, CHF2, —O(Cj-5 aliphatic), C3-C5 cycloalkyl, or C4-C6 heterocycloalkyl containing one oxygen atom.

Exemplary embodiments include H, methyl, ethyl, i-propyl, t-butyl, F. Cl, CF3, CHF2, —OCH3, —OCH2CH3, —O-(i-[propyl), —O-(t-butyl), cyclopropyl, or oxetanyl. More preferably, R1' is H. Or, R1' is methyl. Or, ethyl. Or, CF3. Or, oxetanyl. In several embodiments $R^{D1}$ is $Z^D R9$, wherein $Z^D$ is selected from CONH, NHCO, SO2NH, SO2N (Ci-6 alkyl), NHSO2, CH2NHSO2, CH2N(CH3)SO2, CH2NHCO, COO, SO2, or CO;

In several examples, RD2 is H, halo, C1-4 alkyl, or C1-4 alkoxy.

A particularly preferred compound of formula V-A-i is

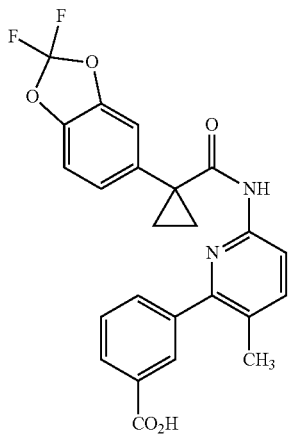 [SMILES: Cc1ccc(NC(=O)C2(c3ccc4c(c3)OC(F)(F)O4)CC2)nc1-c1cccc(C(=O)O)c1]

3-(6-(1-(2,2-difluorobenzo[d][1,3]dioxol-5-yl)cyclopropanecarboxamido)-3-methylpyridin-2-yl)benzoic acid (hereinafter Compound U) or a pharmaceutically acceptable salt thereof.

In another embodiment, the present invention provide CFTR correctors for the use in the treatment of genetic disorders affecting striated muscle selected from sarcoglycanopathies, Brody's disease (BD) and the recessive forms of Cathecolaminergic Polymorphic Ventricular Tachycardia (CPVT) which are selected from:

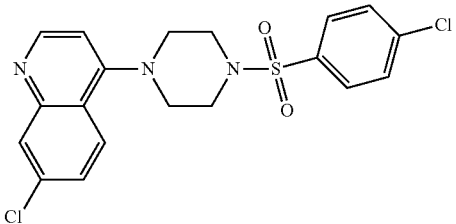 [SMILES: O=S(=O)(c1ccc(Cl)cc1)N1CCN(c2ccnc3cc(Cl)ccc23)CC1]

7-chloro-4-(4-(4-chlorophenylsulfonyl)piperazin-1-yl)quinoline (hereinafter Compound F);

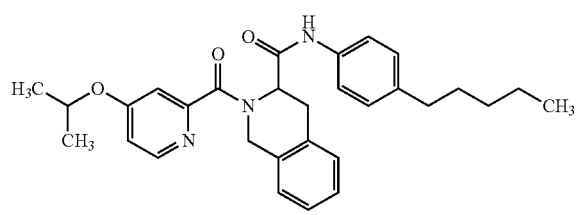 [SMILES: CCCCCc1ccc(NC(=O)C2Cc3ccccc3CN2C(=O)c2cc(OC(C)C)ccn2)cc1]

2-(4-isopropoxypicolinoyl)-N-(4-pentylphenyl)-1,2,3,4-tetrahydroisoquinoline-3-carboxamide (hereinafter Compound L);

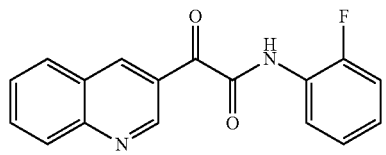 [SMILES: O=C(Nc1ccccc1F)C(=O)c1cnc2ccccc2c1]

N-(2-fluorophenyl)-2-(1H-indol-3-yl)-2-oxoacetamide; (hereinafter Compound M);

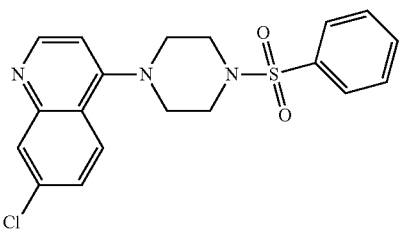 [SMILES: O=S(=O)(c1ccccc1)N1CCN(c2ccnc3cc(Cl)ccc23)CC1]

7-chloro-4-(4-(phenylsulfonyl)piperazin-1-yl)quinoline (hereinafter Compound N);

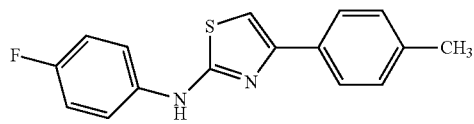

N-(4-fluorophenyl)-4-p-tolylthiazol-2-amine (hereinafter Compound P);

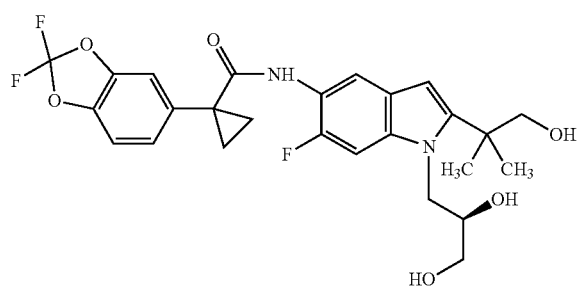 [SMILES: CC(C)(CO)c1cc2cc(NC(=O)C3(c4ccc5c(c4)OC(F)(F)O5)CC3)c(F)cc2n1C[C@@H](O)CO]

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (hereinafter Compound V); or a pharmaceutically acceptable salt thereof.

Compounds of the invention may be administered as a pharmaceutically acceptable salt. These pharmaceutically acceptable salts may be prepared in situ during the final isolation and purification of the compound, or by separately reacting the purified compound, or a non-pharmaceutically acceptable salt thereof, with a suitable base or acid. For a review on suitable salts see Berge et al., *J. Pharm. Sci.*, 1977, 66, 1-19.

Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Compounds Preparation

The compounds for use according to the invention may be made by a variety of methods, including standard chemistry. Certain of the compounds for use according to the invention are well known and readily available from chemical supply houses. Thus for example, Compound A may be prepared according to the procedure as described in WO 2009051909.

Compound B and C and may be prepared according to the procedure as described in WO200411104.

Compound D may be prepared according to the procedure as described in WO 2007021982.

Compounds E, H, I, P, Q, R, S and T may be prepared according to the procedure as described in WO2006101740.

Compound L may be prepared according to the procedure as described in US20050176761.

Compound M may be prepared according to the procedure as described in WO2006699256.

Compounds U and V may be prepared according to the procedures as described in WO2007056341 and WO2007117715 respectively.

Alternatively certain compounds for use according to the invention are commercially available such as for example Compounds F, H, I, N O, P, Q, R, S, T, U and V are available from Exclusive Chemistry Ltd, Selleckchem or Medchem Express LLC.

Methods of Use

The methods of treatment of the invention comprise administering a safe and effective amount of a corrector of CFTR to a patient in need thereof.

A corrector of CFTR according to the invention may be administered by any suitable route of administration, in particular oral administration.

A corrector of CFTR according to the invention may be administered according to a dosing regimen wherein a number of doses are administered at varying intervals of time for a given period of time. For example, doses may be administered one, two, three, or four times per day.

Doses may be administered until the desired therapeutic effect is achieved or indefinitely to maintain the desired therapeutic effect. Suitable dosing regimens, including the duration such regimens are administered, may depend on the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

In one aspect, the invention provides a CFTR corrector for use in the treatment of genetic disorders affecting striated muscle selected from sarcoglycanopathies, Brody's disease (BD) and the recessive forms of Cathecolaminergic Polymorphic Ventricular Tachycardia (CPVT).

In one aspect, the invention provides a CFTR corrector for use in the treatment of genetic disorders affecting striated muscle selected from sarcoglycanopathies, and Brody's disease (BD).

In one aspect, the invention provides a CFTR corrector for use in the treatment of sarcoglycanopathies.

In one aspect, the invention provides a CFTR corrector for use in the treatment of, Brody's disease (BD).

In one aspect, the invention provides a CFTR corrector for use in the recessive forms of Cathecolaminergic Polymorphic Ventricular Tachycardia (CPVT).

In one embodiment, the invention provides the use of a CFTR corrector in the manufacture of a medicament for the treatment of genetic disorders affecting striated muscle selected from sarcoglycanopathies, Brody's disease (BD) and the recessive forms of Cathecolaminergic Polymorphic Ventricular Tachycardia (CPVT).

In one embodiment, the invention provides the use of a CFTR corrector in the manufacture of a medicament for the treatment of genetic disorders affecting striated muscle selected from sarcoglycanopathies and Brody's disease (BD).

In a further embodiment, the invention provides a method of treatment of genetic disorders affecting striated muscle selected from sarcoglycanopathies, Brody's disease (BD) and the recessive forms of Cathecolaminergic Polymorphic Ventricular Tachycardia (CPVT) comprising administering a safe and effective amount of a CFTR corrector to a patient in need thereof.

In a further embodiment, the invention provides a method of treatment of genetic disorders affecting striated muscle selected from sarcoglycanopathies, Brody's disease (BD) comprising administering a safe and effective amount of a CFTR corrector to a patient in need thereof.

In one embodiment, the invention provides a CFTR corrector selected from:

N-(2-(5-chloro-2-methoxyphenylamino)-4'-methyl-4,5'-bithiazol-2'-yl)pivalamide (Compound A);

4-Cyclohexyloxy-2-{1-[4-(4-methoxy-benzensulfonyl)-piperazin-1-yl]-ethyl}-quinazoline (Compound B);

2-{1-[4-(4-Chloro-benzensulfonyl)-piperazin-1-yl]-ethyl}-4-piperidin-1-yl-quinazoline (Compound C);

1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);

N-[2-(5-Chloro-2-methoxy-phenylamino)-4'-methyl-[4,5'] bithiazolyl-2'-yl]-benzamide (Compound E);

7-chloro-4-(4-(4-chlorophenylsulfonyl)piperazin-1-yl)quinoline (Compound F);

4,5,7-trimethyl-N-phenylquinolin-2-amine (Compound H);

N-(4-bromophenyl)-4-methylquinolin-2-amine (Compound I);

2-(4-isopropoxypicolinoyl)-N-(4-pentylphenyl)-1,2,3,4-tetrahydroisoquinoline-3-carboxamide (Compound L);

N-(2-fluorophenyl)-2-(1H-indol-3-yl)-2-oxoacetamide (Compound M);

7-chloro-4-(4-(phenylsulfonyl)piperazin-1-yl)quinoline (Compound N);

N-(4-fluorophenyl)-4-p-tolylthiazol-2-amine (Compound P);
N-(2-(3-acetylphenylamino)-4'-methyl-4,5'-bithiazol-2'-yl) benzamide (Compound Q);
N-(2'-(2-methoxyphenylamino)-4'-methyl-4,5'-bithiazol-2-yl)benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T);
3-(6-(I-(2,2-difluorobenzo[d][1,3]dioxol-5-yl)cyclopropanecarboxamido)-3-methylpyridin-2-yl)benzoic acid (Compound U);
(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound V);

for use in the treatment of genetic disorders affecting striated muscle selected from sarcoglycanopathies, Brody's disease (BD) and the recessive forms of Cathecolaminergic Polymorphic Ventricular Tachycardia (CPVT).

In one embodiment, the invention provides a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5'] bithiazolyl-2'-yl]-benzamide (Compound E);
7-chloro-4-(4-(4-chlorophenylsulfonyl)piperazin-1-yl)quinoline (Compound F);
4,5,7-trimethyl-N-phenylquinolin-2-amine (Compound H);
N-(4-bromophenyl)-4-methylquinolin-2-amine (Compound I);
2-(4-isopropoxypicolinoyl)-N-(4-pentylphenyl)-1,2,3,4-tetrahydroisoquinoline-3-carboxamide (Compound L);
N-(2-fluorophenyl)-2-(1H-indol-3-yl)-2-oxoacetamide (Compound M);
7-chloro-4-(4-(phenylsulfonyl)piperazin-1-yl)quinoline (Compound N);
N-(4-fluorophenyl)-4-p-tolylthiazol-2-amine (Compound P);
N-(2-(3-acetylphenylamino)-4'-methyl-4,5'-bithiazol-2'-yl)-benzamide (Compound Q);
N-(2'-(2-methoxyphenylamino)-4'-methyl-4,5'-bithiazol-2-yl)-benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T);
3-(6-(I-(2,2-difluorobenzo[d][1,3]dioxol-5-yl)cyclopropanecarboxamido)-3-methylpyridin-2-yl)benzoic acid (Compound U);
(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound V);

or pharmaceutically acceptable salt thereof for use in the treatment of genetic disorders affecting striated muscle selected from sarcoglycanopathies, Brody's disease (BD) and the recessive forms of Cathecolaminergic Polymorphic Ventricular Tachycardia (CPVT).

In one embodiment, the invention provides a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5'] bithiazolyl-2'-yl]-benzamide (Compound E);
7-chloro-4-(4-(4-chlorophenylsulfonyl)piperazin-1-yl)quinoline (Compound F);
4,5,7-trimethyl-N-phenylquinolin-2-amine (Compound H);
N-(4-bromophenyl)-4-methylquinolin-2-amine (Compound I);
N-(2-(3-acetylphenylamino)-4'-methyl-4,5'-bithiazol-2'-yl) benzamide (Compound Q);
N-(2'-(2-methoxyphenylamino)-4'-methyl-4,5'-bithiazol-2-yl)benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T); for use in the treatment of genetic disorders affecting striated muscle selected from sarcoglycanopathies and Brody's disease (BD)

In one embodiment, the invention provides a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5'] bithiazolyl-2'-yl]-benzamide (Compound E);
7-chloro-4-(4-(4-chlorophenylsulfonyl)piperazin-1-yl)quinoline (Compound F);
4,5,7-trimethyl-N-phenylquinolin-2-amine (Compound H);
N-(4-bromophenyl)-4-methylquinolin-2-amine (Compound I);
N-(2-(3-acetylphenylamino)-4'-methyl-4,5'-bithiazol-2'-yl) benzamide (Compound Q);
N-(2'-(2-methoxyphenylamino)-4'-methyl-4,5'-bithiazol-2-yl)benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T);

or pharmaceutically acceptable salt thereof for use in the treatment of genetic disorders affecting striated muscle selected from sarcoglycanopathies and Brody's disease (BD).

In one embodiment, the invention provides the use of a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);

N-[2-(5-Chloro-2-methoxy-phenylamino)-4'-methyl-[4,5']bithiazolyl-2'-yl]-benzamide (Compound E);
7-chloro-4-(4-(4-chlorophenylsulfonyl)piperazin-1-yl)quinoline (Compound F) in the manufacture of a medicament in the treatment of genetic disorders affecting striated muscle selected from sarcoglycanopathies, Brody's disease (BD) and the recessive forms of Cathecolaminergic Polymorphic Ventricular Tachycardia (CPVT).

In one embodiment, the invention provides the use of a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5'] bithiazolyl-2'-yl]-benzamide (Compound E);
7-chloro-4-(4-(4-chlorophenylsulfonyl)piperazin-1-yl)quinoline (Compound F);
4,5,7-trimethyl-N-phenylquinolin-2-amine (Compound H);
N-(4-bromophenyl)-4-methylquinolin-2-amine (Compound I);
2-(4-isopropoxypicolinoyl)-N-(4-pentylphenyl)-1,2,3,4-tetrahydroisoquinoline-3-carboxamide (Compound L);
N-(2-fluorophenyl)-2-(1H-indol-3-yl)-2-oxoacetamide (Compound M);
7-chloro-4-(4-(phenylsulfonyl)piperazin-1-yl)quinoline (Compound N);
N-(4-fluorophenyl)-4-p-tolylthiazol-2-amine (Compound P);
N-(2-(3-acetylphenylamino)-4'-methyl-4,5'-bithiazol-2'-yl)-benzamide (Compound Q);
N-(2'-(2-methoxyphenylamino)-4'-methyl-4,5'-bithiazol-2-yl)-benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T);
3-(6-(I-(2,2-difluorobenzo[d][1,3]dioxol-5-yl)cyclopropanecarboxamido)-3-methylpyridin-2-yl)benzoic acid (Compound U);
(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound V)
or a pharmaceutically acceptable salt thereof in the manufacture of a medicament in the treatment of genetic disorders affecting striated muscle selected from sarcoglycanopathies and Brody's disease (BD) and the recessive forms of Cathecolaminergic Polymorphic Ventricular Tachycardia (CPVT).

In one embodiment, the invention provides the use of a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5'] bithiazolyl-2'-yl]-benzamide (Compound E);
7-chloro-4-(4-(4-chlorophenylsulfonyl)piperazin-1-yl)quinoline (Compound F);
4,5,7-trimethyl-N-phenylquinolin-2-amine (Compound H);
N-(4-bromophenyl)-4-methylquinolin-2-amine (Compound I);
2-(4-isopropoxypicolinoyl)-N-(4-pentylphenyl)-1,2,3,4-tetrahydroisoquinoline-3-carboxamide (Compound L);
N-(2-fluorophenyl)-2-(1H-indol-3-yl)-2-oxoacetamide (Compound M); 7-chloro-4-(4-(phenylsulfonyl)piperazin-1-yl)quinoline (Compound N);
N-(4-fluorophenyl)-4-p-tolylthiazol-2-amine (Compound P);
N-(2-(3-acetylphenylamino)-4'-methyl-4,5'-bithiazol-2'-yl)-benzamide (Compound Q);
N-(2'-(2-methoxyphenylamino)-4'-methyl-4,5'-bithiazol-2-yl)-benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T);
3-(6-(I-(2,2-difluorobenzo[d][1,3]dioxol-5-yl)cyclopropanecarboxamido)-3-methylpyridin-2-yl)benzoic acid (Compound U);
(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound V);
in the manufacture of a medicament in the treatment of genetic disorders affecting striated muscle selected from sarcoglycanopathies and Brody's disease (BD) and the recessive forms of Cathecolaminergic Polymorphic Ventricular Tachycardia (CPVT).

In one embodiment, the invention provides the use of a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5'] bithiazolyl-2'-yl]-benzamide (Compound E);
7-chloro-4-(4-(4-chlorophenylsulfonyl)piperazin-1-yl)quinoline (Compound F);
4,5,7-trimethyl-N-phenylquinolin-2-amine (Compound H);
N-(4-bromophenyl)-4-methylquinolin-2-amine (Compound I);
N-(2-(3-acetylphenylamino)-4'-methyl-4,5'-bithiazol-2'-yl) benzamide (Compound Q);
N-(2'-(2-methoxyphenylamino)-4'-methyl-4,5'-bithiazol-2-yl)benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T);
in the manufacture of a medicament in the treatment of genetic disorders affecting striated muscle selected from sarcoglycanopathies and Brody's disease (BD).

In one embodiment, the invention provides the use of a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);

1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);

N-[2-(5-Chloro-2-methoxy-phenylamino)-4'-methyl-[4,5']bithiazolyl-2'-yl]-benzamide (Compound E);

7-chloro-4-(4-(4-chlorophenylsulfonyl)piperazin-1-yl)quinoline (Compound F);

4,5,7-trimethyl-N-phenylquinolin-2-amine (Compound H);

N-(4-bromophenyl)-4-methylquinolin-2-amine (Compound I);

N-(2-(3-acetylphenylamino)-4'-methyl-4,5'-bithiazol-2'-yl)benzamide (Compound Q);

N-(2'-(2-methoxyphenylamino)-4'-methyl-4,5'-bithiazol-2-yl)benzamide (Compound R);

N-phenyl-4-(4-vinylphenyl)thiazol-2-amine (Compound S);

2-(6-methoxy-4-methylquinazolin-2-ylamino)-5,6-dimethylpyrimidin-4(1H)-one (Compound T);

or a salt thereof in the manufacture of a medicament in the treatment of genetic disorders affecting striated muscle selected from sarcoglycanopathies and Brody's disease (BD).

In a further embodiment, the invention provides a method of treating of genetic disorders affecting striated muscle selected from sarcoglycanopathies, Brody's disease (BD) and the recessive forms of Cathecolaminergic Polymorphic Ventricular Tachycardia (CPVT) comprising administering a safe and effective amount of N-(2-(5-chloro-2-methoxyphenylamino)-4'-methyl-4,5'-bithiazol-2'-yl)pivalamide (Compound A);

4-Cyclohexyloxy-2-{1-[4-(4-methoxy-benzensulfonyl)-piperazin-1-yl]-ethyl}-quinazoline (Compound B);

2-{1-[4-(4-Chloro-benzensulfonyl)-piperazin-1-yl]-ethyl}-4-piperidin-1-yl-quinazoline (Compound C);

1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);

N-[2-(5-Chloro-2-methoxy-phenylamino)-4'-methyl-[4,5']bithiazolyl-2'-yl]-benzamide (Compound E);

7-chloro-4-(4-(4-chlorophenylsulfonyl)piperazin-1-yl)quinoline (Compound F) to a patient in need thereof.

In a further embodiment, the invention provides a method of treating of genetic disorders affecting striated muscle selected from sarcoglycanopathies, Brody's disease (BD) and the recessive forms of Cathecolaminergic Polymorphic Ventricular Tachycardia (CPVT) comprising administering a safe and effective amount of N-(2-(5-chloro-2-methoxyphenylamino)-4'-methyl-4,5'-bithiazol-2'-yl)pivalamide (Compound A);

4-Cyclohexyloxy-2-{1-[4-(4-methoxy-benzensulfonyl)-piperazin-1-yl]-ethyl}-quinazoline (Compound B);

2-{1-[4-(4-Chloro-benzensulfonyl)-piperazin-1-yl]-ethyl}-4-piperidin-1-yl-quinazoline (Compound C);

1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);

N-[2-(5-Chloro-2-methoxy-phenylamino)-4'-methyl-[4,5']bithiazolyl-2'-yl]-benzamide (Compound E);

7-chloro-4-(4-(4-chlorophenylsulfonyl)piperazin-1-yl)quinoline (Compound F);

4,5,7-trimethyl-N-phenylquinolin-2-amine (Compound H);

N-(4-bromophenyl)-4-methylquinolin-2-amine (Compound I);

2-(4-isopropoxypicolinoyl)-N-(4-pentylphenyl)-1,2,3,4-tetrahydroisoquinoline-3-carboxamide (Compound L);

N-(2-fluorophenyl)-2-(1H-indol-3-yl)-2-oxoacetamide (Compound M);

7-chloro-4-(4-(phenylsulfonyl)piperazin-1-yl)quinoline (Compound N);

N-(4-fluorophenyl)-4-p-tolylthiazol-2-amine (Compound P);

N-(2-(3-acetylphenylamino)-4'-methyl-4,5'-bithiazol-2'-yl)benzamide (Compound Q);

N-(2'-(2-methoxyphenylamino)-4'-methyl-4,5'-bithiazol-2-yl)benzamide (Compound R);

N-phenyl-4-(4-vinylphenyl)thiazol-2-amine (Compound S);

2-(6-methoxy-4-methylquinazolin-2-ylamino)-5,6-dimethylpyrimidin-4(1H)-one (Compound T);

3-(6-(I-(2,2-difluorobenzo[d][1,3]dioxol-5-yl)cyclopropanecarboxamido)-3-methylpyridin-2-yl)benzoic acid (Compound U);

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound V) to a patient in need thereof.

In a further embodiment, the invention provides a method of treating of genetic disorders affecting striated muscle selected from sarcoglycanopathies, Brody's disease (BD) and the recessive forms of Cathecolaminergic Polymorphic Ventricular Tachycardia (CPVT) comprising administering a safe and effective amount of N-(2-(5-chloro-2-methoxyphenylamino)-4'-methyl-4,5'-bithiazol-2'-yl)pivalamide (Compound A);

4-Cyclohexyloxy-2-{1-[4-(4-methoxy-benzensulfonyl)-piperazin-1-yl]-ethyl}-quinazoline (Compound B);

2-{1-[4-(4-Chloro-benzensulfonyl)-piperazin-1-yl]-ethyl}-4-piperidin-1-yl-quinazoline (Compound C);

1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);

N-[2-(5-Chloro-2-methoxy-phenylamino)-4'-methyl-[4,5']bithiazolyl-2'-yl]-benzamide (Compound E);

7-chloro-4-(4-(4-chlorophenylsulfonyl)piperazin-1-yl)quinoline (Compound F);

4,5,7-trimethyl-N-phenylquinolin-2-amine (Compound H);

N-(4-bromophenyl)-4-methylquinolin-2-amine (Compound I);

2-(4-isopropoxypicolinoyl)-N-(4-pentylphenyl)-1,2,3,4-tetrahydroisoquinoline-3-carboxamide (Compound L);

N-(2-fluorophenyl)-2-(1H-indol-3-yl)-2-oxoacetamide (Compound M);

7-chloro-4-(4-(phenylsulfonyl)piperazin-1-yl)quinoline (Compound N);

N-(4-fluorophenyl)-4-p-tolylthiazol-2-amine (Compound P);

N-(2-(3-acetylphenylamino)-4'-methyl-4,5'-bithiazol-2'-yl)benzamide (Compound Q);

N-(2'-(2-methoxyphenylamino)-4'-methyl-4,5'-bithiazol-2-yl)benzamide (Compound R);

N-phenyl-4-(4-vinylphenyl)thiazol-2-amine (Compound S);

2-(6-methoxy-4-methylquinazolin-2-ylamino)-5,6-dimethylpyrimidin-4(1H)-one (Compound T);

3-(6-(I-(2,2-difluorobenzo[d][1,3]dioxol-5-yl)cyclopropanecarboxamido)-3-methylpyridin-2-yl)benzoic acid (Compound U);

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound V);

or a pharmaceutically acceptable salt thereof to a patient in need thereof.

In a further embodiment, the invention provides a method of treating of genetic disorders affecting striated muscle selected from sarcoglycanopathies, Brody's disease (BD)

comprising administering a safe and effective amount of N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5'] bithiazolyl-2'-yl]-benzamide (Compound E);
7-chloro-4-(4-(4-chlorophenylsulfonyl)piperazin-1-yl)quinoline (Compound F);
4,5,7-trimethyl-N-phenylquinolin-2-amine (Compound H);
N-(4-bromophenyl)-4-methylquinolin-2-amine (Compound I);
N-(2-(3-acetylphenylamino)-4'-methyl-4,5'-bithiazol-2'-yl)benzamide (Compound Q);
N-(2'-(2-methoxyphenylamino)-4'-methyl-4,5'-bithiazol-2-yl)benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T) to a patient in need thereof.

In a further embodiment, the invention provides a method of treating of genetic disorders affecting striated muscle selected from sarcoglycanopathies, Brody's disease (BD) comprising administering a safe and effective amount of N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5'] bithiazolyl-2'-yl]-benzamide (Compound E);
7-chloro-4-(4-(4-chlorophenylsulfonyl)piperazin-1-yl)quinoline (Compound F);
4,5,7-trimethyl-N-phenylquinolin-2-amine (Compound H);
N-(4-bromophenyl)-4-methylquinolin-2-amine (Compound I);
N-(2-(3-acetylphenylamino)-4'-methyl-4,5'-bithiazol-2'-yl)benzamide (Compound Q);
N-(2'-(2-methoxyphenylamino)-4'-methyl-4,5'-bithiazol-2-yl)benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T);
or a pharmaceutically acceptable salt thereof to a patient in need thereof.

In a further embodiment, the invention provides a method of treating of genetic disorders affecting striated muscle selected from sarcoglycanopathies and Brody's disease (BD) comprising administering a safe and effective amount of N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5'] bithiazolyl-2'-yl]-benzamide (Compound E);
7-chloro-4-(4-(4-chlorophenylsulfonyl)piperazin-1-yl)quinoline (Compound F) or a pharmaceutically acceptable salt thereof to a patient in need thereof.

Compositions

CFTR correctors may be formulated into a pharmaceutical composition prior to administration to a patient.

Accordingly, in one aspect the invention is directed to pharmaceutical compositions comprising a CFTR corrector and one or more pharmaceutically acceptable excipients for use in the treatment of genetic disorders affecting striated muscle selected from sarcoglycanopathies, Brody's disease (BD) and the recessive forms of Cathecolaminergic Polymorphic Ventricular Tachycardia (CPVT).

In one embodiment, the invention is directed to pharmaceutical compositions comprising a CFTR corrector and one or more pharmaceutically acceptable excipients for use in the treatment of genetic disorders affecting striated muscle selected from sarcoglycanopathies and Brody's disease (BD)

In one embodiment, the invention is directed to pharmaceutical compositions comprising a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5'] bithiazolyl-2'-yl]-benzamide (Compound E);
7-chloro-4-(4-(4-chlorophenylsulfonyl)piperazin-1-yl)quinoline (Compound F)
4,5,7-trimethyl-N-phenylquinolin-2-amine (Compound H);
N-(4-bromophenyl)-4-methylquinolin-2-amine (Compound I);
2-(4-isopropoxypicolinoyl)-N-(4-pentylphenyl)-1,2,3,4-tetrahydroisoquinoline-3-carboxamide (Compound L);
N-(2-fluorophenyl)-2-(1H-indol-3-yl)-2-oxoacetamide (Compound M);
7-chloro-4-(4-(phenylsulfonyl)piperazin-1-yl)quinoline (Compound N);
N-(4-fluorophenyl)-4-p-tolylthiazol-2-amine (Compound P);
N-(2-(3-acetylphenylamino)-4'-methyl-4,5'-bithiazol-2'-yl)benzamide (Compound Q);
N-(2'-(2-methoxyphenylamino)-4'-methyl-4,5'-bithiazol-2-yl)benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T);
3-(6-(I-(2,2-difluorobenzo[d][1,3]dioxol-5-yl)cyclopropanecarboxamido)-3-methylpyridin-2-yl)benzoic acid (Compound U);
(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound V) and one or more pharmaceutically acceptable excipients for use in the treatment of genetic disorders affecting striated muscle selected from sarcoglycanopathies, Brody's disease (BD) and the recessive forms of Cathecolaminergic Polymorphic Ventricular Tachycardia (CPVT).

In another embodiment, the invention is directed to pharmaceutical compositions comprising a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5']bithiazolyl-2'-yl]-benzamide (Compound E);
7-chloro-4-(4-(4-chlorophenylsulfonyl)piperazin-1-yl)quinoline (Compound F)
4,5,7-trimethyl-N-phenylquinolin-2-amine (Compound H);
N-(4-bromophenyl)-4-methylquinolin-2-amine (Compound I);
2-(4-isopropoxypicolinoyl)-N-(4-pentylphenyl)-1,2,3,4-tetrahydroisoquinoline-3-carboxamide (Compound L);
N-(2-fluorophenyl)-2-(1H-indol-3-yl)-2-oxoacetamide (Compound M);
7-chloro-4-(4-(phenylsulfonyl)piperazin-1-yl)quinoline (Compound N);
N-(4-fluorophenyl)-4-p-tolylthiazol-2-amine (Compound P);
N-(2-(3-acetylphenylamino)-4'-methyl-4,5'-bithiazol-2'-yl)benzamide (Compound Q);
N-(2'-(2-methoxyphenylamino)-4'-methyl-4,5'-bithiazol-2-yl)benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T);
3-(6-(I-(2,2-difluorobenzo[d][1,3]dioxol-5-yl)cyclopropanecarboxamido)-3-methylpyridin-2-yl)benzoic acid (Compound U);
(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound V); or a pharmaceutically acceptable salt thereof and one or more pharmaceutically acceptable excipients for use in the treatment of genetic disorders affecting striated muscle selected from sarcoglycanopathies, Brody's disease (BD) and the recessive forms of Cathecolaminergic Polymorphic Ventricular Tachycardia (CPVT).

In another embodiment, the invention is directed to pharmaceutical compositions comprising a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5']bithiazolyl-2'-yl]-benzamide (Compound E);
7-chloro-4-(4-(4-chlorophenylsulfonyl)piperazin-1-yl)quinoline (Compound F) and one or more pharmaceutically acceptable excipients for use in the treatment of genetic disorders affecting striated muscle selected from sarcoglycanopathies, Brody's disease (BD) and the recessive forms of Cathecolaminergic Polymorphic Ventricular Tachycardia (CPVT).

In another embodiment, the invention is directed to pharmaceutical compositions comprising a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5']bithiazolyl-2'-yl]-benzamide (Compound E);
7-chloro-4-(4-(4-chlorophenylsulfonyl)piperazin-1-yl)quinoline (Compound F) or a pharmaceutically acceptable salt thereof and one or more pharmaceutically acceptable excipients for use in the treatment of genetic disorders affecting striated muscle selected from sarcoglycanopathies, Brody's disease (BD) and the recessive forms of Cathecolaminergic Polymorphic Ventricular Tachycardia (CPVT).

In another embodiment, the invention is directed to pharmaceutical compositions comprising a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5']bithiazolyl-2'-yl]-benzamide (Compound E);
7-chloro-4-(4-(4-chlorophenylsulfonyl)piperazin-1-yl)quinoline (Compound F)
4,5,7-trimethyl-N-phenylquinolin-2-amine (Compound H);
N-(4-bromophenyl)-4-methylquinolin-2-amine (Compound I);
N-(2-(3-acetylphenylamino)-4'-methyl-4,5'-bithiazol-2'-yl)benzamide (Compound Q);
N-(2'-(2-methoxyphenylamino)-4'-methyl-4,5'-bithiazol-2-yl)benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T) and one or more pharmaceutically acceptable excipients for use in the treatment of genetic disorders affecting striated muscle selected from sarcoglycanopathies and Brody's disease (BD).

In another embodiment, the invention is directed to pharmaceutical compositions comprising a CFTR corrector selected from:
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzensulfonyl)-piperazin-1-yl]-ethyl}-quinazoline (Compound B);
2-{1-[4-(4-Chloro-benzensulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5']bithiazolyl-2'-yl]-benzamide (Compound E);

7-chloro-4-(4-(4-chlorophenylsulfonyl)piperazin-1-yl)quinoline (Compound F)
4,5,7-trimethyl-N-phenylquinolin-2-amine (Compound H);
N-(4-bromophenyl)-4-methylquinolin-2-amine (Compound I);
N-(2-(3-acetylphenylamino)-4'-methyl-4,5'-bithiazol-2'-yl)benzamide (Compound Q);
N-(2'-(2-methoxyphenylamino)-4'-methyl-4,5'-bithiazol-2-yl)benzamide (Compound R);
N-phenyl-4-(4-vinylphenyl)thiazol-2-amine (Compound S);
2-(6-methoxy-4-methylquinazolin-2-ylamino)-5,6-dimethylpyrimidin-4(1H)-one (Compound T) or a pharmaceutically acceptable salt thereof and one or more pharmaceutically acceptable excipients for use in the treatment of genetic disorders affecting striated muscle selected from sarcoglycanopathies and Brody's disease (BD).

CFTR correctors according to the invention are capable of existing in stereoisomeric forms. It will be understood that the compounds of use according to the invention encompasses all geometric and optical isomers of these compounds and the mixtures thereof including racemates.

CFTR correctors according to the invention and the pharmaceutically acceptable excipient or excipients will typically be formulated into a dosage form adapted for administration to the patient by the desired route of administration. For example, dosage forms include those adapted for oral administration such as tablets, capsules, caplets, pills, troches, powders, syrups, elixirs, suspensions, solutions, emulsions, sachets, and cachets), or those adapted for inhalation such as aerosols, solutions, and dry powders.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of a CFTR corrector thereof once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavour masking agents, colouring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions for use according to the invention are prepared using techniques and methods known to those skilled in the art. Some of the methods commonly used in the art are described in *Remington's Pharmaceutical Sciences* (Mack Publishing Company).

A pharmaceutical composition comprising a CFTR corrector may be prepared by, for example, admixture at ambient temperature and atmospheric pressure.

In one aspect, the composition for use according to the invention is a solid oral dosage form such as a tablet or capsule comprising a safe and effective amount of a CFTR corrector and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, *acacia*, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

CFTR correctors may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of use according to the invention or a pharmaceutically acceptable salt thereof may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

CFTR correctors according to the invention may be formulated for parenteral administration by bolus injection or continuous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

In another aspect, the composition for use according to the invention is a liquid oral dosage form. Oral liquids such as solution, syrups and elixirs can be prepared in dosage unit form so that a given quantity contains a predetermined amount of a CFTR corrector. Syrups can be prepared by dissolving a compound of use according to the invention or a pharmaceutically acceptable salt thereof in a suitably flavored aqueous solution, while elixirs are prepared through the use of a non-toxic alcoholic vehicle. Suspensions can be formulated by dispersing a compound of use according to the invention or a pharmaceutically acceptable salt thereof in a non-toxic vehicle.

Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added. The compound of use according to the invention or its pharmaceutically acceptable salts may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

In another aspect, the invention is directed to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In a further embodiment, the invention is directed to a dosage form adapted for administration to a patient by inhalation via a nebulizer.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 µg-10 mg of the compound of use according to the invention or a pharmaceutically acceptable salt thereof.

According to the invention, a CFTR corrector may be used in combination with one or more other therapeutic agents, in the treatment of genetic disorders affecting striated muscle selected from sarcoglycanopathies, Brody's disease (BD) and the recessive forms of Cathecolaminergic Polymorphic Ventricular Tachycardia (CPVT).

Biological Data
In Vitro Results

The following examples illustrate the invention without limiting the scope thereof.

Example 1

HEK293 cells expressing different α-SG mutants have been treated with the Compounds A, B, C, D, E, F, H, I, Q, R, S and T according to protocols developed in CF studies [Loo and Clarke 2011; Becq et al 2011, Pedemonte et al 2005; Wang et al 2006]. Concentration and time-dependent recovery of treated mutants have been evaluated by Western blotting. The proteasome inhibitor MG132, at the concentration of 10 µM, or DMSO at 1‰ concentration, have been used as positive and negative control, respectively.

In FIG. 1 the result obtained by treating cells expressing the R98H mutant of α-SG for 24 hours with Compound C 5 µM, Compound B 10 µM, Compound E 10 µM, Compound F 10 µM, Compound A 2 µM, Compound D 10 µM are shown. At the end of treatments, cells were lysed and total proteins resolved by SDS-PAGE. Western blotting has been performed by using α-SG specific antibody and β-actin specific antibody, used to normalize loaded proteins (in FIG. 1, upper panel, a representative experiment is shown). The expression of α-SG in different samples has been determined by densitometric analysis of the western blotting experiments and indicated as percentage of the protein present in cells expressing the R98H mutant treated with DMSO (negative control). The graph in the lower part of FIG. 1 shows the average values (+/− standard error) of three independent experiments. All the compounds tested induce the recovery of the mutant to an extent comparable to that obtained by proteasomal inhibition (MG132 treated D98H expressing cells).

Figure 4:
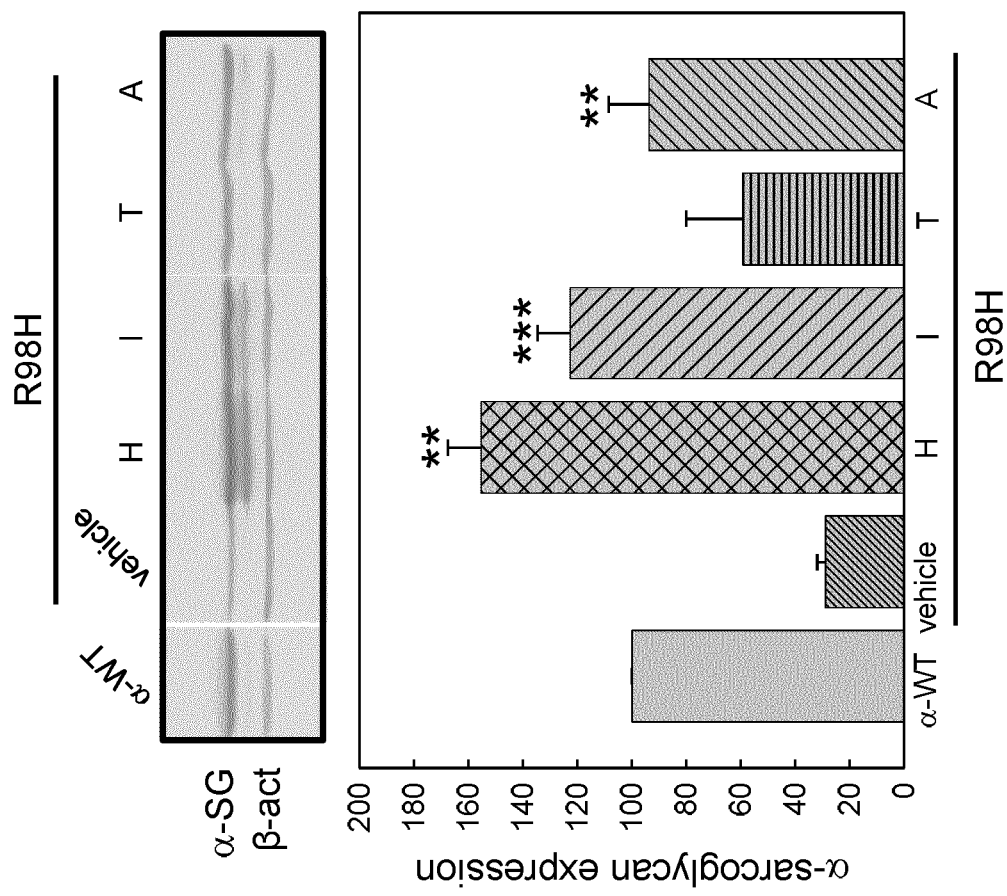
FIG. 4 CFTR correctors (Compounds H, I, T and A) promote the rescue of R98H mutant of alpha-sarcoglycan in HEK293 cell model. Alpha-sarcoglycan protein level has been determined by western blot (a representative experiment is shown in the top panel) on total protein content purified from cells expressing the R98H mutant treated with either compound H 15 µM, I 10 µM, T 15 µM, and A 2 µM (as indicated), or DMSO (vehicle), used as negative control. Cells expressing the wild type form of alpha-sarcoglycan (α-WT) have been analyzed for comparison. Blot has been probed with α-sarcoglycan (α-SG) specific antibody. To normalize protein content, the expression of β-actin (β-act) has been used as an internal marker. The graph in the lower part of the figure shows the average values (+/− standard error) of alpha-sarcoglycan expression determined by densitometric analyses of at least three independent experiments. Values are expressed as percentage of the alpha-sarcoglycan protein content present in untreated cells expressing the WT protein. *, P≤0.001; , P≤0.01.

In FIG. 4 the result obtained by treating cells expressing the R98H mutant of α-SG for 24 hours with either Compound H 15 µM, Compound I 10 µM, Compound T 15 µM, Compound A 2 µM, or DMSO at 1‰ concentration, used as negative control, are shown. Cells expressing the wild type form of α-sarcoglycan have been used for comparison. At the end of treatments, cells were lysed and total proteins resolved by SDS-PAGE. Western blotting has been performed by using α-SG specific antibody and β-actin specific antibody, used to normalize loaded proteins (in upper panel of FIG. 4, a representative experiment is shown). The expression of α-SG in different samples has been determined by densitometric analysis of the western blotting experiments and indicated as percentage of the protein present in cells expressing the wild type form of α-sarcoglycan. The graph in the lower part of FIG. 4 shows the average values (+/− standard error) of at least three independent experiments. The compounds tested induced the recovery of the R98H mutant to levels that in some cases were even greater than those present in HEK cells expressing the wild type protein.

Figure 5:
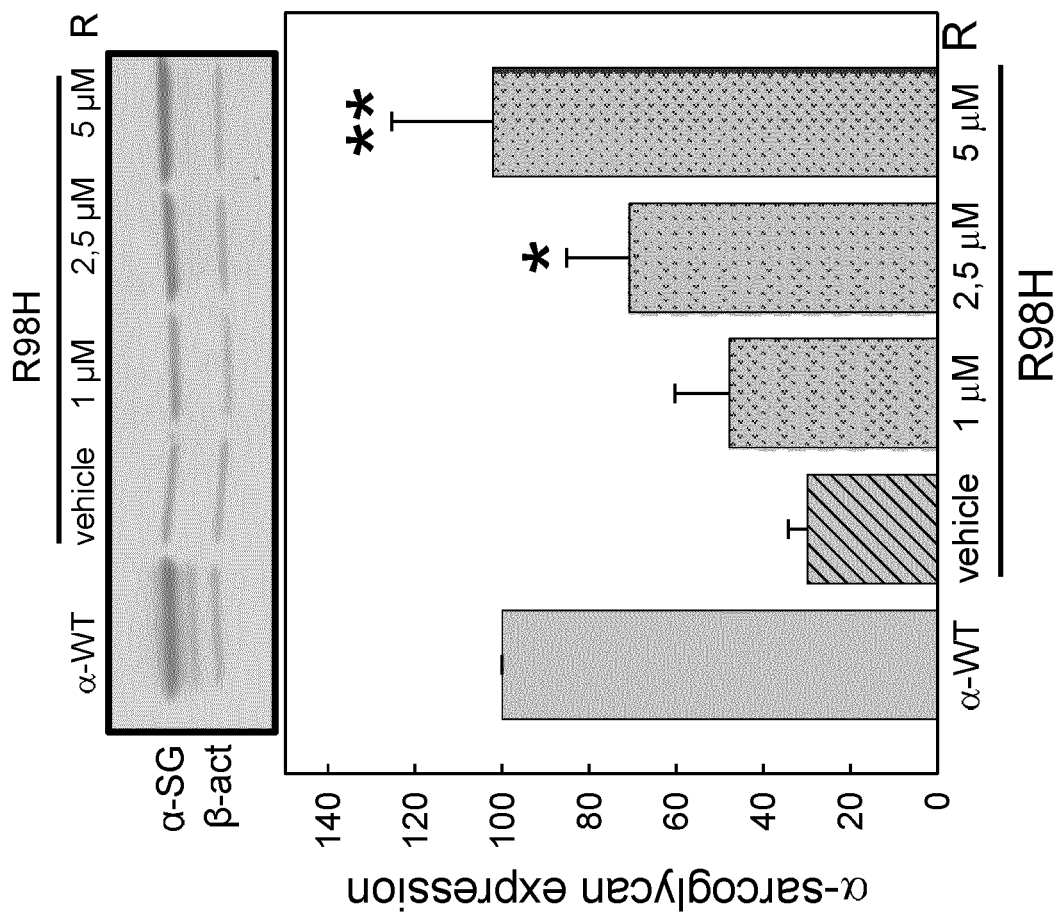
FIG. 5 The Compound R promotes the rescue of R98H mutant of alpha-sarcoglycan in HEK293 cell model in dose dependent manner. Alpha-sarcoglycan protein level has been determined by western blot (a representative experiment is shown in the top panel) on total protein content purified from cells expressing the R98H mutant treated with either increasing concentrations (as indicated) of compound R, or DMSO (vehicle) used as negative control. Cells expressing the wild type form of alpha-sarcoglycan (α-WT) have been analyzed, for comparison. Blot has been probed with α-sarcoglycan (α-SG) specific antibody. To normalize protein content, the expression of β-actin (β-act) has been used as an internal marker. The graph in the lower part of the figure shows the average values (+/− standard error) of alpha-sarcoglycan expression determined by densitometric analyses of at least three independent experiments. Values are expressed as percentage of the alpha-sarcoglycan protein content present in untreated cells expressing the WT protein. **, $P \leq 0.01$; *, $P \leq 0.05$.

In FIG. 5 the result obtained by treating cells expressing the R98H mutant of α-SG for 24 hours with either increasing concentration of Compound R (1, 2.5, 5 µM) or DMSO at 1‰ concentration, used as negative control, are shown. Cells expressing the wild type form of α-sarcoglycan have been used for comparison. At the end of treatments, cells were lysed and total proteins resolved by SDS-PAGE. Western blotting has been performed by using α-SG specific antibody and β-actin specific antibody, used to normalize loaded proteins (in upper panel of FIG. 5, a representative experiment is shown). The expression of α-SG in different samples has been determined by densitometric analysis of western blotting experiments and indicated as percentage of the protein present in cells expressing the wild type form of α-sarcoglycan. The graph in the lower part of FIG. 5 shows the average values (+/− standard error) of at least three independent experiments. The R compound induced a dose dependent recovery of the R98H mutant that, at the highest concentration (5 µM), reached the level of the wild type protein.

Figure 6:
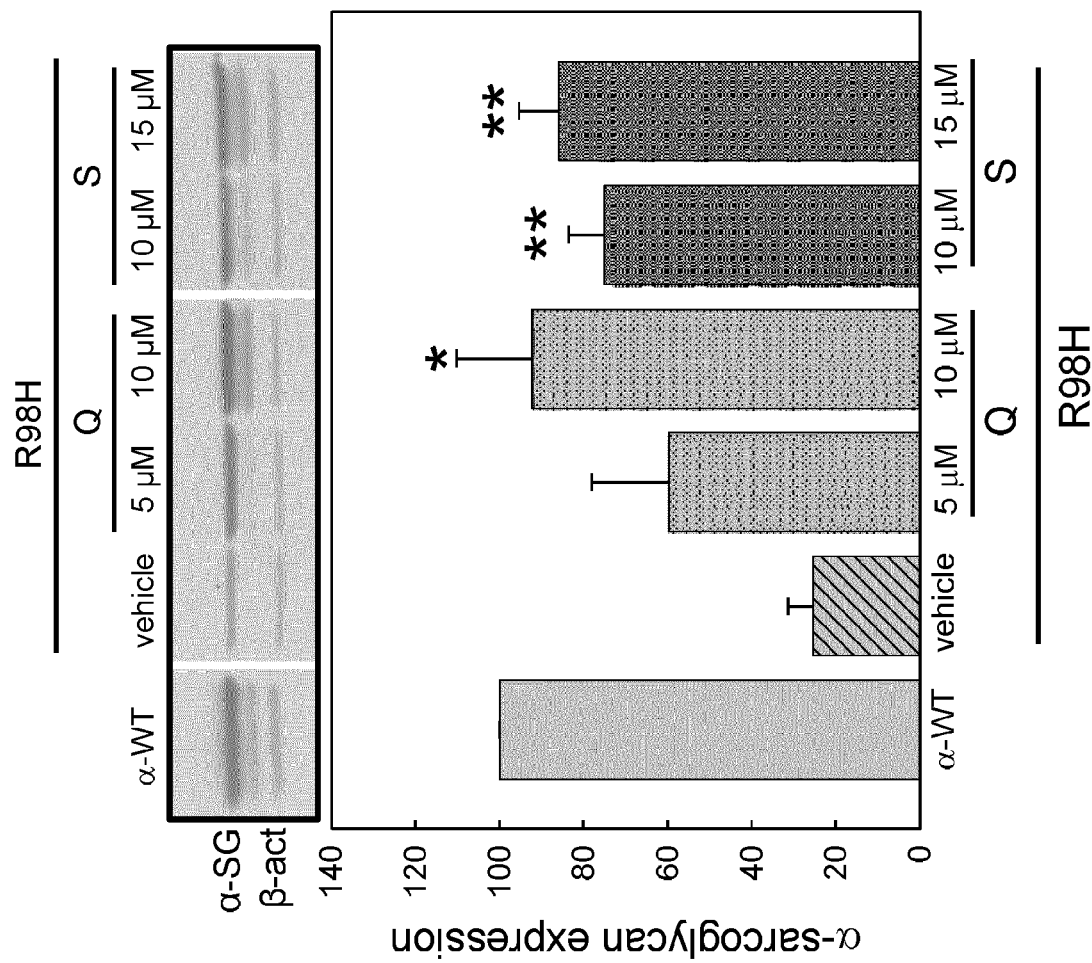
FIG. 6 Compounds Q and S promote the rescue of R98H mutant of alpha-sarcoglycan in HEK293 cell model in dose dependent manner. Alpha-sarcoglycan protein level has been determined by western blot (a representative experiment is shown in the top panel) on total protein content purified from cells expressing the R98H mutant treated with either increasing concentrations (as indicated) of compounds Q and S, or DMSO (vehicle) used as negative control. Cells expressing the wild type form of alpha-sarcoglycan (α-WT) have been analyzed, for comparison. Blot has been probed with α-sarcoglycan (α-SG) specific antibody. To normalize protein content, the expression of β-actin (β-act) has been used as an internal marker. The graph in the lower part of the figure shows the average values (+/− standard error) of alpha-sarcoglycan expression determined by densitometric analyses of at least three independent experiments. Values are expressed as percentage of the alpha-sarcoglycan protein content present in untreated cells expressing the WT protein. **, $P \leq 0.01$; *, $P \leq 0.05$.

In FIG. 6 the result obtained by treating cells expressing the R98H mutant of α-SG for 24 hours with either increasing concentration of Compound Q (5, 10 µM), increasing concentration of Compound S (10, 15 µM) or DMSO at 1‰ concentration, used as negative control, are shown. Cells expressing the wild type form of α-sarcoglycan have been used for comparison. At the end of treatments, cells were lysed and total proteins resolved by SDS-PAGE. Western blotting has been performed by using α-SG specific antibody and β-actin specific antibody, used to normalize loaded proteins (in upper panel of FIG. 6, a representative experiment is shown). The expression of α-SG in different samples has been determined by densitometric analysis of western blotting experiments and indicated as percentage of the protein present in cells expressing the wild type form of α-sarcoglycan. The graph in the lower part of FIG. 6 shows the average values (+/− standard error) of at least three independent experiments. Both Q and S compounds induced a dose dependent recovery of the R98H mutant that, at the highest concentrations, reached the level of the wild type protein.

Figure 7:
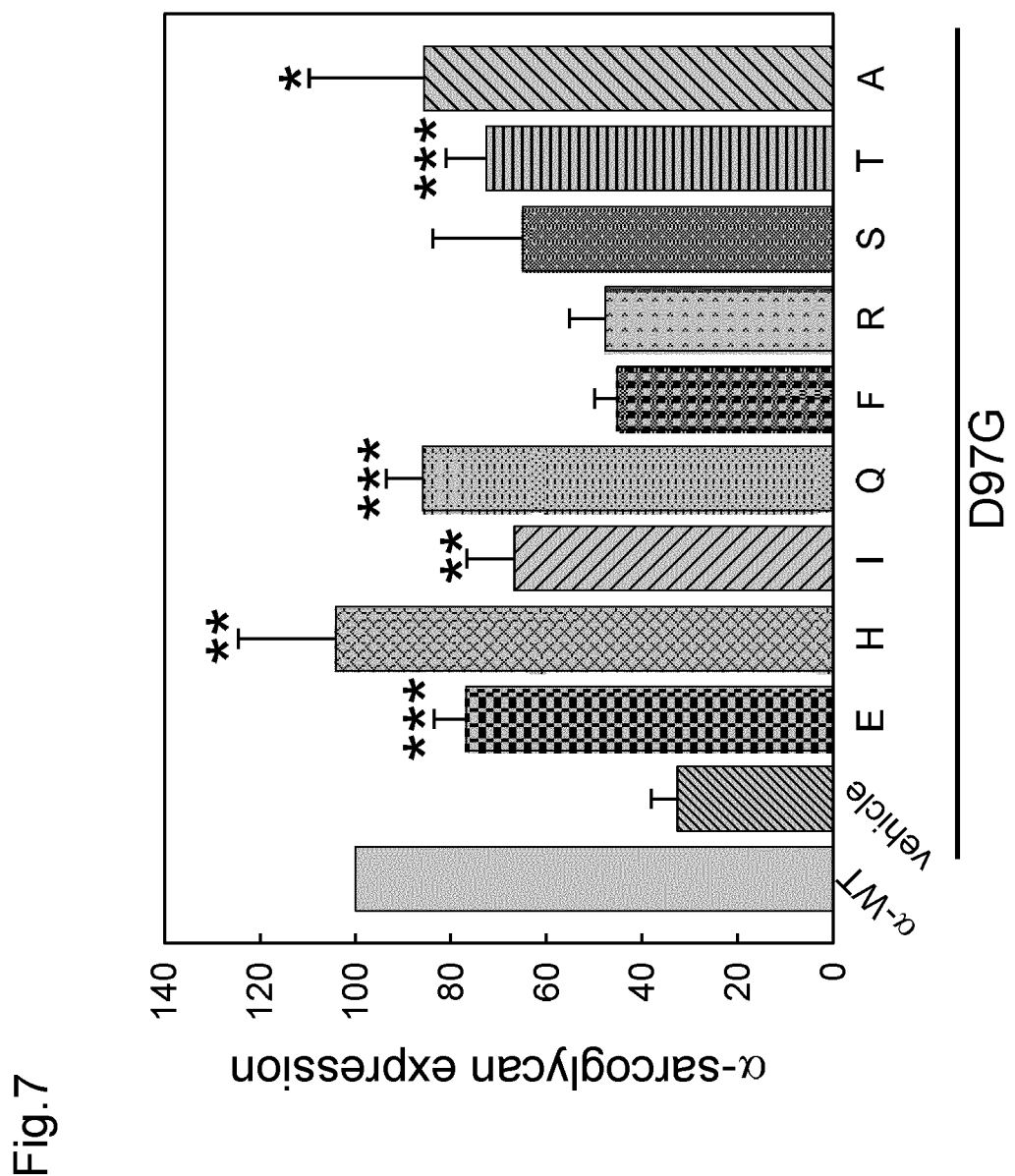
FIG. 7 CFTR correctors (Compounds E, H, I, Q, F, R, S, T and A) promote the rescue of D97G mutant of alpha-sarcoglycan in HEK293 cell model. Alpha-sarcoglycan protein level has been determined by western blot on total protein content purified from cells expressing the D97G mutant treated with either compound E 10 μM, H 15 μM, I 10 μM, Q 10 μM, F 10 μM, R 5 μM, S 15 μM, T 15 μM, and A 2 μM (as indicated), or DMSO (vehicle) used as negative control. Cells expressing the wild type form of alpha-sarcoglycan (α-WT) have been analyzed for comparison. The graph shows the average values (+/− standard error) of alpha-sarcoglycan expression determined by densitometric analyses of at least three independent experiments. Values are expressed as percentage of the alpha-sarcoglycan protein content present in untreated cells expressing the WT protein. *, $P \leq 0.001$; , $P \leq 0.01$; *, $P \leq 0.05$.

In FIG. 7 is shown the content of α-sarcoglycan protein present in HEK cells transfected with the D97G mutant of α-SG treated for 24 hours with either Compound E 10 μM, Compound H 15 μM, Compound I 10 μM, Compound Q 10 μM, Compound F 10 μM, Compound R 5 μM, Compound S 15 μM, Compound T 15 μM, Compound A 2 μM, or DMSO at 1‰ concentration, used as negative control, are shown. Cells expressing the wild type form of α-sarcoglycan have been used for comparison. At the end of treatments, cells were lysed and total proteins resolved by SDS-PAGE. Western blotting has been performed by using α-SG specific antibody and β-actin specific antibody, used to normalize loaded proteins. The expression of α-SG in different samples has been determined by densitometric analysis of western blotting experiments and indicated as percentage of the protein present in cells expressing the wild type form of α-sarcoglycan. The graph of FIG. 7 shows the average values (+/− standard error) of at least three independent experiments. The compounds tested induce the recovery of the D97G mutant that in some cases reached the level present in HEK cells expressing the wild type protein.

Example 2

The cellular localization of either the V247M or R98H mutants, upon corrector treatments, has been verified by confocal immunofluorescence.

Figure 2:
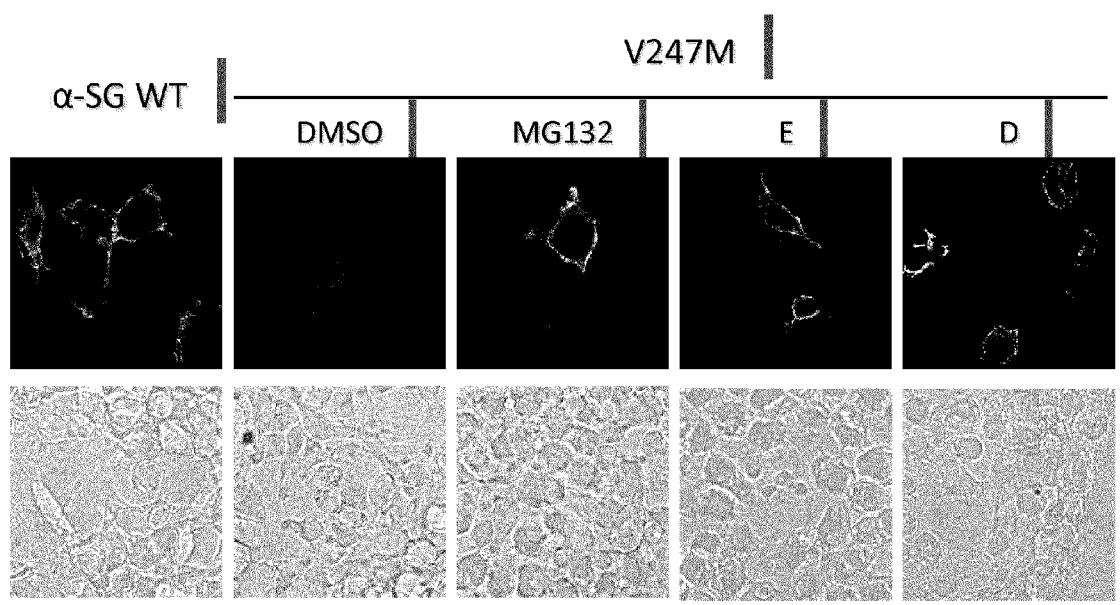
FIG. 2 CFTR correctors (Compounds E and D) promote the correct membrane localization of V247M alpha-sarcoglycan in HEK293 cells. Cells expressing the V247M mutant of alpha-sarcoglycan cultivated on glass coverslips have been treated with either correctors vehicle (DMSO) used as negative control, MG132 used as positive control, compound E and compound D. Cells expressing the wild type form of alpha-sarcoglycan have also been utilized (α-SG WT) for comparison. After treatments, intact cells have been immunodecorated with an antibody specific for an extracellular epitope of alpha-sarcoglycan in order to mark only the membrane resident protein. The bounded antibody has been visualized by a secondary antibody conjugated with the fluorescence dye TRITC. Images have been recorder with a Leica laser scanning confocal microscope. Behind each fluorescence image, the same field collected in transmission light, is reported.

In the experiment reported in FIG. 2, HEK 293 cells expressing the V247M mutant have been treated for 24 hours with either Compound E (10 μM) or Compound D (10 μM), MG132 (positive control) or DMSO at 1‰ concentration (negative control). At the end of treatments, not permeabilized cells were incubated with a monoclonal antibody specific for an extracellular epitope of α-sarcoglycan in order to mark only the membrane resident α-sarcoglycan. By comparison, cells expressing the wild type form of α-sarcoglycan have also been used. Laser scanning microscopy analysis shows that, in the absence of drug treatment (DMSO) the wild type form of α-sarcoglycan correctly localized at the plasmamembrane, whereas only traces of the mutant protein were visible on the cell surface. As previously demonstrated, proteasomal inhibition (MG132), by reducing the degradation of mutant protein, promoted V247M membrane localization (Gastaldello et al 2008). Treatments with compound E and D promoted the correct plasma membrane localization of the V247M mutant as well.

Figure 8:
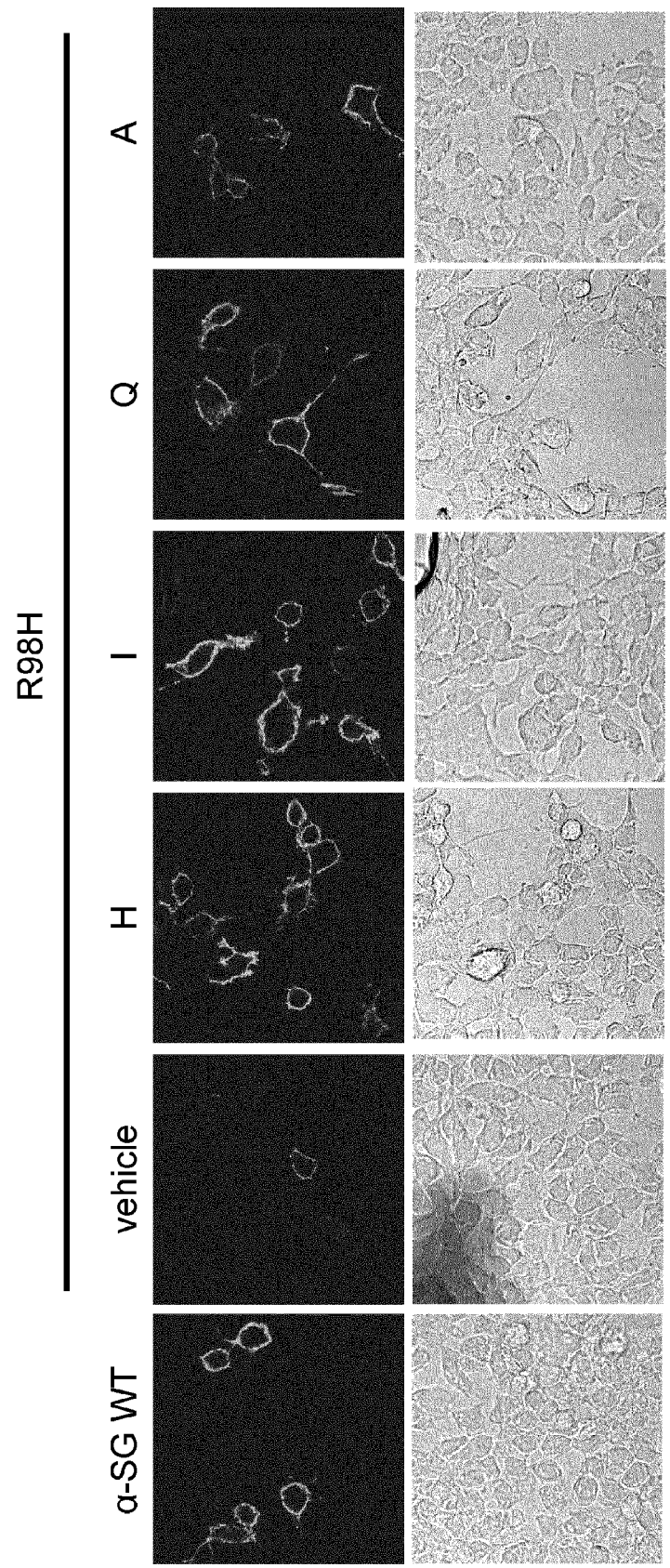
FIG. 8 Compounds H, I, Q, and A promote the correct membrane localization of R98H alpha-sarcoglycan in HEK293 cells. Cells expressing the R98H mutant of alpha-sarcoglycan cultivated on glass coverslips have been treated with either DMSO (vehicle) used as negative control, or compound H 15 μM, I 10 μM, Q 10 μM and A 2 μM, for 24 hours. Cells expressing the wild type form of alpha-sarcoglycan (α-SG WT) have been utilized for comparison. After treatments, intact cells have been immunodecorated with an antibody specific for an extracellular epitope of alpha-sarcoglycan in order to mark only the membrane resident protein. Membrane-bound antibodies have been visualized by a secondary antibody conjugated with the fluorescence dye TRITC. Images have been recorded, at the same magnification, with a Leica laser scanning confocal microscope. Behind each fluorescence image, the same field collected in transmission light, is reported to estimate the number of cells present.

In the experiment reported in FIG. 8, HEK 293 cells expressing the R98H mutant have been treated for 24 hours with either Compound H (15 μM), Compound I (10 μM), Compound Q (10 μM), Compound A (2 μM) or the vehicle DMSO at 1‰ concentration used as negative control. By comparison, cells expressing the wild type form of α-sarcoglycan have also been used. At the end of treatments, not permeabilized cells were incubated with a monoclonal antibody specific for an extracellular epitope of α-sarcoglycan in order to mark only the membrane resident α-sarcoglycan. Laser scanning microscopy analysis shows that, the wild type form of α-sarcoglycan correctly localized at the plasma-membrane. In the absence of treatment (vehicle) only traces of the R98H mutant protein were visible on the cell surface whereas, treatments with the indicated compounds promoted the correct plasma-membrane localization of the mutant protein.

Figure 9:
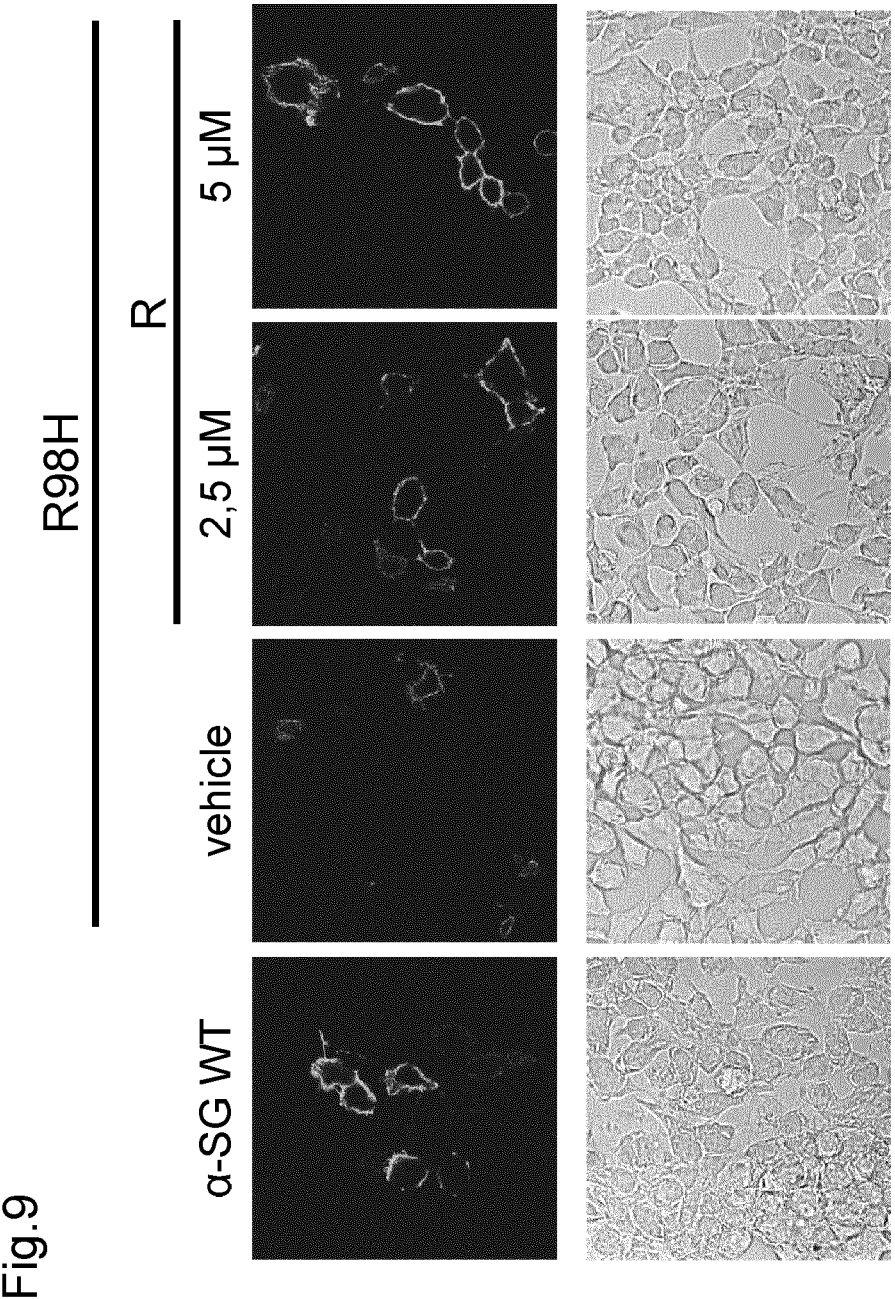
FIG. 9 Compound R promote the correct membrane localization of R98H alpha-sarcoglycan in HEK293 cells. Cells expressing the R98H mutant of alpha-sarcoglycan cultivated on glass coverslips have been treated with either DMSO (vehicle), used as negative control, or compound R at different concentrations (as indicated), for 24 hours. Cells expressing the wild type form of alpha-sarcoglycan (α-SG WT) have been utilized for comparison. After treatments, intact cells have been immunodecorated with an antibody specific for an extracellular epitope of alpha-sarcoglycan in order to mark only the membrane resident protein. Membrane-bound antibodies have been visualized by a secondary antibody conjugated with the fluorescence dye TRITC. All images have been recorded, at the same magnification, with a Leica laser scanning confocal microscope. Behind each fluorescence image, the same field collected in transmission light, is reported to estimate the number of cells present.

In the experiment reported in FIG. 9, HEK 293 cells expressing the R98H mutant have been treated for 24 hours with either two different concentration of Compound R (2.5 and 5 μM), or the vehicle DMSO at 1‰ concentration used as negative control. By comparison, cells expressing the wild type form of α-sarcoglycan have also been used. At the end of treatments, not permeabilized cells were incubated with a monoclonal antibody specific for an extracellular epitope of α-sarcoglycan in order to mark only the membrane resident α-sarcoglycan. Laser scanning microscopy analysis shows that, the wild type form of α-sarcoglycan correctly localized at the plasma-membrane. In the absence of treatment (vehicle) only traces of the R98H mutant protein were visible on the cell surface whereas, treatments with the compound R promoted the correct plasma-membrane localization of the mutant protein.

Example 3

Recently, a muscular disorder defined congenital pseudomyotonia (PMT), has been described in Chianina cattle. In affected animals, PMT is due to a missense mutation in ATP2A1 gene (R164H) that causes a drastic reduction of SERCA1 protein [Sacchetto et al. 2009]. Genetic and biochemical data have indicated that Chianina PMT is the true counterpart of human BD and it could represent a suitable, non-conventional, animal model for the investigation of the pathogenesis of BD.

Figure 3:
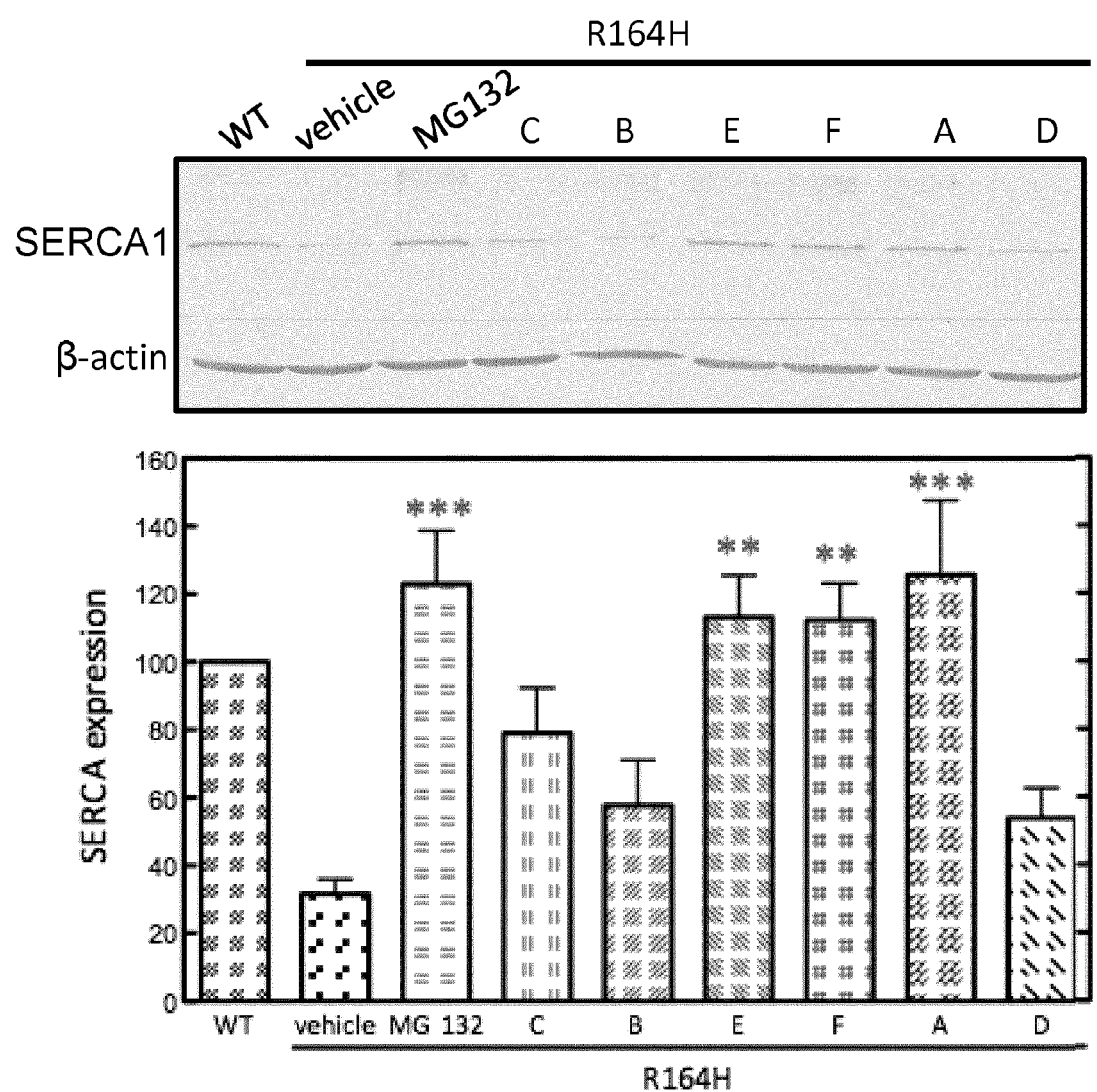
FIG. 3 CFTR correctors (Compounds A to F) promote the rescue of R164H mutant of SERCA1 in HEK293 cells. SERCA1 protein level has been determined by western blot (a representative experiment is shown in the top panel) on total protein of lysates from HEK 293 cells expressing the R164H mutant treated with either CFTR correctors (compound A, B, C, D, E and F as indicated), MG132 or correctors vehicle (DMSO). Cells expressing the wild type form of SERCA1 have also been utilized, for comparison. To normalized protein loading, the expression of β-actin has been used as an internal marker. The graph in the lower part of the figure shows the average values (+/− standard error) of SERCA1 expression determined by densitometric analyses of at least three independent experiments. Values are expressed as percentage of the SERCA protein content present in cells expressing the wild type form. *, P≤0.001; , P≤0.01.

In FIG. 3 are reported the results obtained with HEK 293 cells expressing the R164H mutant of SERCA1 treated for 24 hours with either Compound C 5 μM, Compound B 10 μM, Compound E 10 μM, compound F 10 μM, Compound A 2 μM, compound D 10 μM, MG132 (proteasome inhibitor) 10 μM, used as positive control or the vehicle DMSO at 1‰ concentration, used as negative control. At the end of treatments, cells were lysed and total protein resolved by SDS-PAGE. Western blotting analysis has been performed by using SERCA1 specific antibody and β-actin specific antibody, to normalize loaded proteins. In the upper panel of FIG. 3 is reported a representative Western blotting experiment. The expression of SERCA1 in different samples has been determined by densitometric analysis and indicated as percentage of SERCA 1 content present in wild type expressing cells treated with DMSO. The densitometric analyses (reported in FIG. 3 lower panel) show that the Compounds tested were able to promote R164H mutant rescue to an extent comparable to that of wild type SERCA1.

Figure 10:
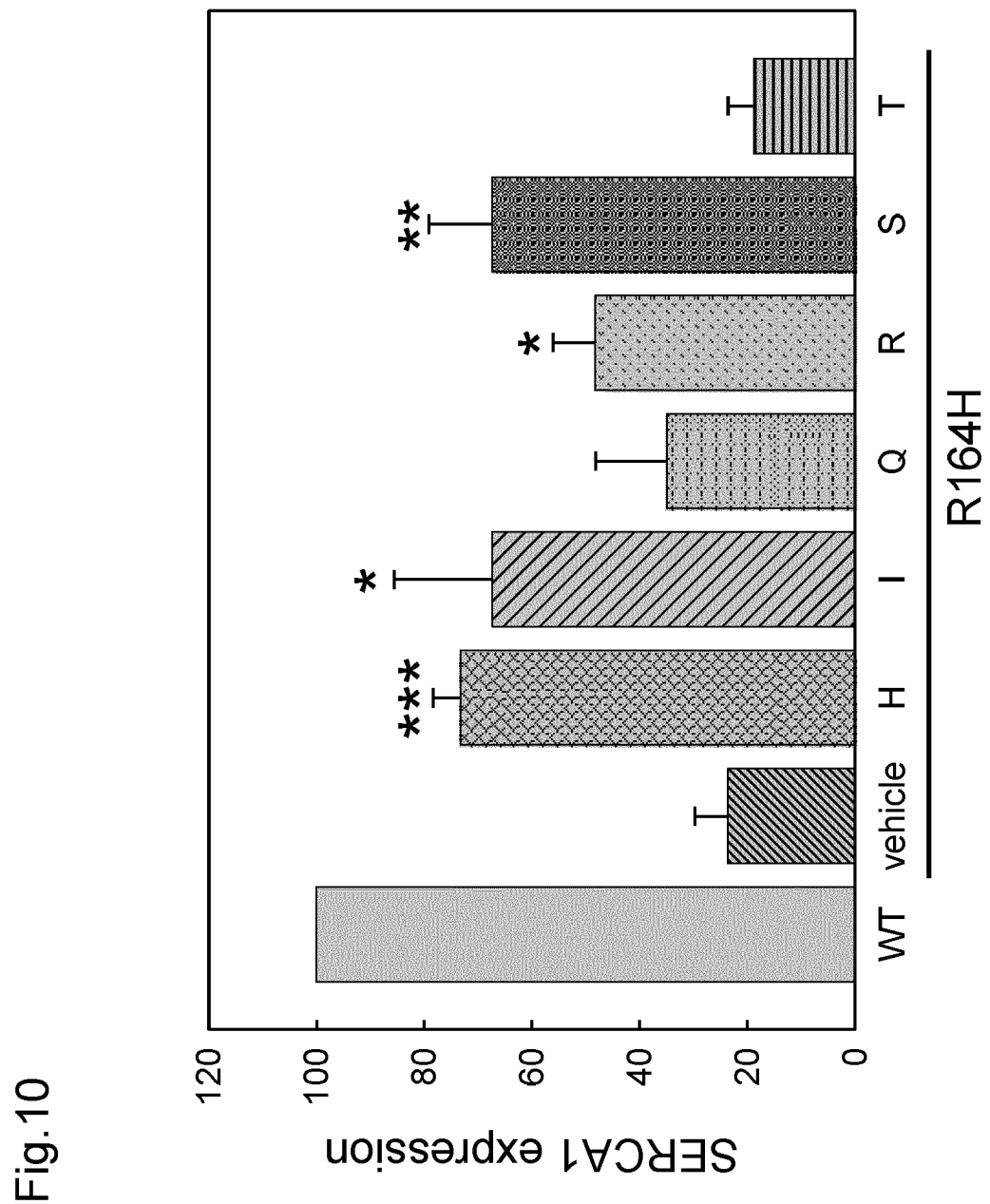
FIG. 10 CFTR correctors (compounds H, I, Q, R, S and T) promote the rescue of R164H mutant of SERCA1 in HEK293 cell model. SERCA1 protein level has been determined by western blot on total protein content purified from cells expressing the R164H mutant treated with either compound H 15 μM, I 10 μM, Q 10 μM, R 5 μM, S 15 μM and T 15 μM (as indicated), or DMSO (vehicle) used as negative control. Cells expressing the wild type form of SERCA1 (WT) have been analyzed for comparison. The graph shows the average values (+/− standard error) of SERCA1 expression determined by densitometric analyses of at least three independent experiments. Values are expressed as percentage of the SERCA1 protein content present in untreated cells expressing the WT protein. *, $P \leq 0.001$; , $P \leq 0.01$; *, $P \leq 0.05$.

In FIG. 10 is reported the content of SERCA1 protein present in HEK 293 cells transfected with the R164H mutant of SERCA1 and treated for 24 hours with either Compound H 15 μM, Compound I 10 μM, compound Q 10 μM, Compound R 5 μM, Compound S 15 μM, Compound T 15 μM or the vehicle DMSO at 1‰ concentration, used as negative control. Cells expressing the wild type form of SERCA1 have also been used for comparison. At the end of treatments, cells were lysed and total protein resolved by SDS-PAGE. Western blotting analysis has been performed by using SERCA1 specific antibody and β-actin specific antibody, to normalize loaded proteins. The expression of SERCA1 in different samples has been determined by densitometric analysis and indicated as percentage of SERCA 1 content present in wild type expressing cells. The graph of FIG. 10 reports the average values (+/− standard error) of at least three independent experiments. The compounds tested were able to promote R164H mutant rescue to an extent that in some cases is comparable to that of wild type SERCA1.

Preclinical Studies

The preclinical effect of a CFTR correctors according to the invention in sarcoglycanopathies can be assessed, for example, in one or more animal models of the diseases as described here below.

As animal model for LGMD2D is available the KO α-SG mice (Liu and Engvall 1999), for LGMD2E the KO β-SG mice (Araishi et al. 1999), for LGMD2C the KO γ-SG mice (Hack et al. 2000) for LGMD2F the KO δ-SG mice (Hack et al. 2000). However these animal models are unsuitable for studying the preclinical effect of the invention as they don't produce the sarcoglycan proteins at all. Knock In (KI) mice, expressing the mutated forms of each sarcoglycan should be necessary. To overcome time consuming and management problems of transgenic mouse production, and, importantly, to easily obtain animals expressing as many different sarcoglycan missense mutations as those necessary for the study, we intend to transduce specific sarcoglycan KO mice with Adeno Associated Viruses (AAVs) expressing either the wild type or the mutant forms of α-SG, β-SG γ-SG and δ-SG. The procedure for AAV production is described in [McClure et al 2011; Shin et al 2012] however virus production is committed to a specialized company, whereas animal transduction is accomplish like described in [Cordier et al 2000; Vitiello et al 2009 Roux-Buisson et al. 2012]

Thus, for example:

Ex vivo experiments are performed on explanted gastrocnemious muscles from sarcoglycanopathy animal models as described above. As described in Assereto et al. 2005, the explanted muscles are quickly cleaned from fat, connective tissue, and blood; divided bundles of about 5-10 muscle fibers and incubated with either a suitable dosage of a CFTR correctors according to the invention, the proteasome inhibitor bortezomib (Velcade) (Gastaldello et al 2008, Bonuccelli et al 2007) used as positive control or drugs vehicle used as negative control. After 24 to 48 hours of treatments, explants are rapidly homogenized and the expression of sarcoglycans is tested by western blotting analyses.

In vivo experiments are performed by localized injection in gastrocnemious muscles of sarcoglycanopathy animal models of either a CFTR corrector or Velcade used as positive control, the contralateral muscles, injected with the drug vehicles, represent the negative control. After treatments, animals are sacrificed and muscles are either rapidly frozen to further immunofluorescent analysis concerning the localization of the rescued sarcoglycans or homogenized and analyzed by western blotting to verify the expression of the mutated proteins.

In vivo experiments are performed by systemic administration of drugs in sarcoglycanopathy animal models thanks to the use of subcutaneously implanted Alzet Minipumps as described in [Bonucelli et al. 2007]. In this case, animals of matched age and sex are treated with either the CFTR correctors, the proteasome inhibitor Velcade (positive control) or the vehicle (negative control). After treatments, animal are sacrificed, limb girdle muscles are rapidly frozen or homogenized and the expression of sarcoglycans are analyzed by western blotting whereas their localization are tested by immunofluorescent analysis. The wild type animals are always used for comparison.

The preclinical effect of a CFTR correctors according to the invention in Brody's disease (BD) can be assessed, for example in the PMT affected Chianina cattle representing the animal model of the disease (housed at the Veterinary Hospital of the University of Padova) [Sacchetto et al. 2009].

Thus, for example:

Ex vivo experiments are performed on freshly isolated biopsies from the semimembranosus muscle of the PMT affected cow. As described in Assereto et al. 2005 bundles of 5-10 muscle fibers are incubated with either a suitable dosage of CFTR correctors according to the invention, the proteasome inhibitor bortezomib (Velcade) used as positive control or the drugs vehicle used as negative controls. After treatments, explants are rapidly homogenized the expression of the different proteins are tested by western blotting analysis whereas the functional recovery of SERCA1 is determined accordingly to (Sacchetto et al 2009)

The preclinical effect of a CFTR correctors according to the invention in the recessive forms of Cathecolaminergic Polymorphic Ventricular Tachycardia (CPVT) can be assessed, for example in CPVT animal models like the Knock In CASQ$^{R33Q/R33Q}$ mice [Rizzi et al. 2008] and the Triadin−/− mice transduced with AAVs expressing either wild type or mutant forms of the cardiac triadin [Roux-Buisson et al. 2012].

Thus, for example:

Ex vivo experiments are performed in explanted hearts from CPVT animal models perfused with either suitable dosages of CFTR correctors according to the invention, the proteasome inhibitor bortezomib (Velcade) used as positive control or the drugs vehicles used as negative controls. After treatments, hearts are rapidly homogenized and the expression of CASQ2, triadin, junction and RyR1 are tested by western blotting analyses.

In vivo experiments are performed by systemic administration of drugs in CPVT animal models subcutaneously implanted with a Alzet Minipumps as described in [Bonucelli et al. 2007]. In this case, animals of matched age and sex are treated with either CFTR correctors, the proteasome inhibitor Velcade (positive control) or the vehicle (negative control). After treatments, animal are sacrificed, hearts, rapidly frozen, are homogenized and the expression of the different proteins are analyzed by western blotting whereas their localization are tested by immunofluorescent analysis. The wild type animals are always used for comparison.

The wild type animals of each pathological model as described above will always be used for comparison.

Propedeutic to plan clinical trials, the effects of CFTR correctors according to the invention in sarcoglycanopathies and Brody's disease can be assessed in primary culture of myoblasts obtained from sarcoglycanopathy and BD affected patients. This possibility is based on the collaborations stated with Prof. G. P. Comi, responsible of the collection of sarcoglycanopathy biopsies stored at the Department of Neurological Sciences, University of Milan and with Dr, G. Vattemi of the Department of Neurological Sciences and Vision, Section of Clinical Neurology, University of Verona. Myoblasts obtained from biopsies of healthy subjects are already available in our laboratory. Myoblasts either from healthy and affected patients will be incubated with either CFTR correctors, the proteasome inhibitor Velcade used as positive control or the drug vehicles used as negative control. Quantitative, topological and functional rescue of sarcoglycans and SERCA1 will be determined by western blotting, immunofluorescence analyses and functional assays.

Clinical Study 1. local treatments: patients with sarcoglycanopathies, BD and CPVT linked to triadin defects, selected according to the clinical phenotype and the type of missense mutations of which they are carriers, are monitored for 30 days before the beginning of the treatment. The conditions of the anterior tibialis muscle receiving treatment, are determined by electromyography and magnetic resonance imaging and a muscle biopsy planned just before the beginning of treatment. Patients are then locally injected in the anterior tibialis muscle with suitable dosage of CFTR correctors according to the invention. At the end of the treatment a biopsy is carried out and muscle samples are used to determine the quantitative recovery and the localization of the rescued of either sarcoglycan, SERCA1, CASQ2, triadin junctin or RyR1 proteins.

2. systemic treatments: patients with sarcoglycanopathies, BD and CPVT are selected and monitored as above described, a suitable dosage of a CFTR correctors according to the invention will be administered. Dose formulation and length of treatments are determined according to the results obtained by local treatments and to the information present in the literature regarding cystic fibrosis treatments, The phenotype improvement are evaluated by clinical investigations (MRI, EMG, ECG, enzyme assays).

REFERENCES

Araishi K, Sasaoka T, Imamura M, Noguchi S, Hama H, Wakabayashi E, Yoshida M, Hori T, Ozawa E. Loss of the sarcoglycan complex and sarcospan leads to muscular dystrophy in beta-sarcoglycan-deficient mice. Hum Mol Genet. 1999, 8:1589-98.

Assereto S, Stringara S, Sotgia F, Bonuccelli G, Broccolini A, Pedemonte M, Traverso M, Biancheri R, Zara F, Bruno C, Lisanti M P, Minetti C. Pharmacological rescue of the dystrophin-glycoprotein complex in Duchenne and Becker skeletal muscle explants by proteasome inhibitor treatment. Am J Physiol Cell Physio 2005, l290:C577-82.

Becq F, Mall M A, Sheppard D N, Conese M, Zegarra-Moran O. Pharmacological therapy for cystic fibrosis: from bench to bedside. J Cyst Fibros 2011, 10 Suppl: S129-145. Review.

Bonuccelli G, Sotgia F, Capozza F, Gazzerro E, Minetti C, Lisanti M P. Localized treatment with a novel FDA-approved proteasome inhibitor blocks the degradation of dystrophin and dystrophin-associated proteins in mdx mice. Cell Cycle. 2007, 6:1242-8.

Cordier L, Hack A A, Scott M O, Barton-Davis E R, Gao G, Wilson J M, McNally E M, Sweeney H L. Rescue of skeletal muscles of gamma-sarcoglycan-deficient mice with adeno-associated virus-mediated gene transfer. Mol Ther. 2000, 1:119-29.

Gastaldello S, D'Angelo S, Franzoso S, Fanin M, Angelini C, Betto R, Sandonà D. Inhibition of proteasome activity promotes the correct localization of disease-causing α-sarcoglycan mutants in HEK-293 cells constitutively expressing β, γ-, and δ-sarcoglycan. Am J Pathol 2008, 173:170-81.

Hack A A, Lam M Y, Cordier L, Shoturma D I, Ly C T, Hadhazy M A, Hadhazy M R, Sweeney H L, McNally E M. Differential requirement for individual sarcoglycans and dystrophin in the assembly and function of the dystrophin-glycoprotein complex. J Cell Sci. 2000, 113 (Pt 14):2535-44.

Liu L A, Engvall E. Sarcoglycan isoforms in skeletal muscle. J Biol Chem 1999, 274:38171-6.

Loo T W, Clarke D M. Repair of CFTR Folding Defects with Correctors that Function as Pharmacological Chaperones. Methods Mol Biol 2011, 741:23-37.

McClure C, Cole K L, Wulff P, Klugmann M, Murray A J. Production and titering of recombinant adeno-associated viral vectors. J Vis Exp. 2011, 57:e3348.

Pedemonte N, Lukacs G L, Du K, Caci E, Zegarra-Moran O, Galietta L J, Verkman A S. Small-molecule correctors of defective DeltaF508-CFTR cellular processing identified by high-throughput screening. J. Clin. Invest. 2005, 115 (9):2564-2571

Rizzi N, Liu N, Napolitano C, Nori A, Turcato F, Colombi B, Bicciato S, Arcelli D, Spedito A, Scelsi M, Villani L, Esposito G, Boncompagni S, Protasi F, Volpe P, Priori S G. Unexpected structural and functional consequences of the R33Q homozygous mutation in cardiac calsequestrin: A complex arrhythmogenic cascade in a knock in mouse model. Circ Res 2008, 103:298-306.

Roux-Buisson N, Cacheux M, Fourest-Lieuvin A, Fauconnier J, Brocard J, Denjoy I, Durand P, Guicheney P, Kyndt F, Leenhardt A, Le Marec H, Lucet V, Mabo P, Probst V, Monnier N, Ray P F, Santoni E, Trémeaux P, Lacampagne A, Fauré J, Lunardi J, Marty I. Absence of triadin, a protein of the calcium release complex, is responsible for cardiac arrhythmia with sudden death in human. Hum Mol Genet. 2012, 21:2759-67.

Sacchetto R, Testoni S. Gentile A. Damiani E, Rossi M, Liguori R, Drögemüller C, Mascarello F. A defective SERCA1 protein is responsible for congenital pseudomyotonia in Chianina cattle. Am J Pathol 2009, 174:565-73.

Shin J H, Yue Y, Duan D. Recombinant adeno-associated viral vector production and purification. Methods Mol Biol. 2012, 798:267-84.

Vitiello C, Faraso S, Sorrentino N C, Di Salvo G, Nusco E, Nigro G, Cutillo L, Calabro R, Auricchio A, Nigro V. Disease rescue and increased lifespan in a model of cardiomyopathy and muscular dystrophy by combined AAV treatments. PLoS One. 2009, 4:e5051.

Wang Y, Bartlett M C, Loo T W, Clarke D M. Specific rescue of cystic fibrosis transmembrane conductance regulator processing mutants using pharmacological chaperones. Mol Pharmacol. 2006, 70(1): 297-302.

The invention claimed is:

1. A method of treating sarcoglycanopathies, comprising administering an effective amount of a CFTR corrector selected from the group consisting of
N-(2-(5-chloro-2-methoxyphenylamino)-4'-methyl-4,5'-bithiazol-2'-yl)pivalamide (Compound A);
4-Cyclohexyloxy-2-{1-[4-(4-methoxy-benzenesulfonyl)-piperazin-1-yl]-ethyl}-quinazoline (Compound B);
2-{1-[4-(4-Chloro-benzenesulfonyl)-piperazin-1-yl]-ethyl}-4-piperidin-1-yl-quinazoline (Compound C);
1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);
N-[2-(5-Chloro-2-methoxy-phenylamino)-4'-methyl-[4,5']bithiazolyl-2'-yl]-benzamide (Compound E);

7-chloro-4-(4-(4-chlorophenylsulfonyl)piperazin-1-yl) quinoline (Compound F);

4,5,7-trimethyl-N-phenylquinolin-2-amine (Compound H);

N-(4-bromophenyl)-4-methylquinolin-2-amine (Compound I);

2-(4-isopropoxypicolinoyl)-N-(4-pentylphenyl)-1,2,3,4-tetrahydroisoquinoline-3-carboxamide (Compound L);

7-chloro-4-(4-(phenylsulfonyl)piperazin-1-yl)quinoline (Compound N);

N-(4-fluorophenyl)-4-p-tolylthiazol-2-amine (Compound P);

N-(2-(3-acetylphenylamino)-4'-methyl-4,5'-bithiazol-2'-yl)benzamide (Compound Q);

N-(2-(2-methoxyphenylamino)-4'-methyl-4,5'-bithiazol-2'-yl)benzamide (Compound R);

N-phenyl-4-(4-vinylphenyl)thiazol-2-amine (Compound S);

2-(6-methoxy-4-methylquinazolin-2-ylamino)-5,6-dimethylpyrimidin-4(1H)-one (Compound T);

3-(6-(1-(2,2-difluorobenzo[d][1,3]dioxol-5-yl) cyclopropanecarboxamide)-3-methylpyridin-2-yl)benzoic acid (Compound U); and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound V);

or a pharmaceutically acceptable salt thereof to a patient in need thereof.

2. A method of treatment as claimed in claim 1, wherein the CFTR corrector is selected from the group consisting of:

N-(2-(5-chloro-2-methoxyphenylamino)-4'-methyl-4,5'-bithiazol-2'-yl)pivalamide (Compound A);

4-Cyclohexyloxy-2-{1-[4-(4-methoxy-benzenesulfonyl)-piperazin-1-yl]-ethyl}-quinazoline (Compound B);

2-{1-[4-(4-Chloro-benzenesulfonyl)-piperazin-1-yl]-ethyl}-4-piperidin-1-yl-quinazoline (Compound C);

1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);

N-[2-(5-Chloro-2-methoxy-phenylamino)-4'-methyl-[4,5']bithiazolyl-2'-yl]-benzamide (Compound E);

7-chloro-4-(4-(4-chlorophenylsulfonyl)piperazin-1-yl) quinoline (Compound F);

4,5,7-trimethyl-N-phenylquinolin-2-amine (Compound H);

N-(4-bromophenyl)-4-methylquinolin-2-amine (Compound I);

N-(2-(3-acetylphenylamino)-4'-methyl-4,5'-bithiazol-2'-yl)benzamide (Compound Q);

N-(2-(2-methoxyphenylamino)-4'-methyl-4,5'-bithiazol-2'-yl)benzamide (Compound R);

N-phenyl-4-(4-vinylphenyl)thiazol-2-amine (Compound S); and 2-(6-methoxy-4-methylquinazolin-2-ylamino)-5,6-dimethylpyrimidin-4(1H)-one (Compound T) or a pharmaceutically acceptable salt thereof.

3. A method of treating sarcoglycanopathies, comprising administering an effective amount of a pharmaceutical composition comprising a CFTR corrector selected from the group consisting of N-(2-(5-chloro-2-methoxyphenylamino)-4'-methyl-4,5'-bithiazol-2'-yl)pivalamide (Compound A);

4-Cyclohexyloxy-2-{1-[4-(4-methoxy-benzenesulfonyl)-piperazin-1-yl]-ethyl}-quinazoline (Compound B);

2-{1-[4-(4-Chloro-benzenesulfonyl)-piperazin-1-yl]-ethyl}-4-piperidin-1-yl-quinazoline (Compound C);

1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);

N-[2-(5-Chloro-2-methoxy-phenylamino)-4'-methyl-[4,5']bithiazolyl-2'-yl]-benzamide (Compound E);

7-chloro-4-(4-(4-chlorophenyl sulfonyl)piperazin-1-yl) quinoline (Compound F);

4,5,7-trimethyl-N-phenylquinolin-2-amine (Compound H);

N-(4-bromophenyl)-4-methylquinolin-2-amine (Compound I);

2-(4-isopropoxypicolinoyl)-N-(4-pentylphenyl)-1,2,3,4-tetrahydroisoquinoline-3-carboxamide (Compound L);

7-chloro-4-(4-(phenyl sulfonyl)piperazin-1-yl)quinoline (Compound N);

N-(4-fluorophenyl)-4-p-tolylthiazol-2-amine (Compound P);

N-(2-(3-acetylphenylamino)-4'-methyl-4,5'-bithiazol-2'-yl)benzamide (Compound Q);

N-(2-(2-methoxyphenylamino)-4'-methyl-4,5'-bithiazol-2'-yl)benzamide (Compound R);

N-phenyl-4-(4-vinylphenyl)thiazol-2-amine (Compound S);

2-(6-methoxy-4-methyl quinazolin-2-ylamino)-5,6-dimethylpyrimidin-4(1H)-one (Compound T);

3-(6-(1-(2,2-difluorobenzo[d][1,3]dioxol-5-yl) cyclopropanecarboxamido)-3-B methylpyridin-2-yl)benzoic acid (Compound U); and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound V);

or a pharmaceutically acceptable salt thereof and one or more pharmaceutically acceptable excipients to a patient in need thereof.

4. A method as claimed in claim 3, wherein the CFTR corrector is selected from the group consisting of:

N-(2-(5-chloro-2-methoxyphenylamino)-4'-methyl-4,5'-bithiazol-2'-yl)pivalamide (Compound A);

4-Cyclohexyloxy-2-{1-[4-(4-methoxy-benzenesulfonyl)-piperazin-1-yl]-ethyl}-quinazoline (Compound B);

2-{1-[4-(4-Chloro-benzenesulfonyl)-piperazin-1-yl]-ethyl}-4-piperidin-1-yl-quinazoline (Compound C);

1-(benzo[d][1,3]dioxol-5-yl)-N-(5-((S)-(2-chlorophenyl)((R)-3-hydroxypyrrolidin-1-yl)methyl)thiazol-2-yl)cyclopropanecarboxamide (Compound D);

N-[2-(5-Chloro-2-methoxy-phenylamino)-4'-methyl-[4,5']bithiazolyl-2'-yl]-benzamide (Compound E);

7-chloro-4-(4-(4-chlorophenylsulfonyl)piperazin-1-yl) quinoline (Compound F);

4,5,7-trimethyl-N-phenylquinolin-2-amine (Compound H);

N-(4-bromophenyl)-4-methylquinolin-2-amine (Compound I);

N-(2-(3-acetylphenylamino)-4'-methyl-4,5'-bithiazol-2'-yl)benzamide (Compound Q);

N-(2'-(2-methoxyphenylamino)-4'-methyl-4,5'-bithiazol-2-yl)benzamide (Compound R);

B  N-phenyl-4-(4-vinylphenyl)thiazol-2-amine (Compound S); and 2-(6-methoxy-4-methylquinazolin-2-ylamino)-5,6-dimethylpyrimidin-4(1H)-one (Compound T); or a pharmaceutically acceptable salt thereof.

\* \* \* \* \*